United States Patent [19]
Willner et al.

[11] Patent Number: 5,443,701
[45] Date of Patent: Aug. 22, 1995

[54] ELECTROBIOCHEMICAL ANALYTICAL METHOD AND ELECTRODES

[75] Inventors: Itamar Willner, Mevasseret-Zion; Evgeny Katz, Jerusalem; Azalia Riklin, Jerusalem; Ron Kasher, Jerusalem; Benjamin Shoham, Jerusalem, all of Israel

[73] Assignee: Yissum Research Development Company of Hebrew University of Jerusalem, Israel

[21] Appl. No.: 109,922

[22] Filed: Aug. 23, 1993

[30] Foreign Application Priority Data

Aug. 25, 1992 [IL] Israel .................................. 102930

[51] Int. Cl.⁶ .................................. G01N 27/26
[52] U.S. Cl. .................................. 204/153.12; 204/415; 204/418; 204/290 R; 204/291; 435/817; 435/288
[58] Field of Search .................... 204/403, 418, 153.21, 204/153.19, 153.12, 415, 290 R, 291; 435/817, 288

[56] References Cited

U.S. PATENT DOCUMENTS 4,964,972 10/1990 Sagiv et al. .......................... 204/418
5,232,574 8/1993 Saika et al. .......................... 204/418

OTHER PUBLICATIONS

Degani et al, *Journal of the American Chemical Society*, 1989 111, pp. 2358–2361.
Heller, *Acc. Chem. Res.*, 1990, 23, 128–134.
Willner, et al, *Journal of the American Chemical Society*, 1990, 112, pp. 6438–6439.
Willner and Lapidot, *Journal of the American Chemical Society* 1991, 113, pp. 3625–3626.
Foulds et al, *Anal. Chem.* 1988, 60, pp. 2473–2478.
Heller, *J. Phys. Chem.* 1992, 96, pp. 3579–3587.
Gorton et al, *Analytica Chimica Acta.*, 1990, 288, pp. 23–30.
Degani et al, *Journal of the American Chemical Society*, 1988, 110, pp. 2615–2620.
Hart, Harold, Organic Chemistry—A Short Course, 1991, 467.

Primary Examiner—John Niebling
Assistant Examiner—Bruce F. Bell
Attorney, Agent, or Firm—Wigman, Cohen, Leitner & Myers

[57] ABSTRACT

An analytical method for determining the presence or concentration of an analyte in a liquid medium is provided in which electrons are transferred from an electrode material of an electrode to the redox center of an enzyme, by the mediation of an electron mediator, whereby in the presence of an analyte the enzyme calalyzed a redox reaction in which the analyte is converted into a product. By measuring either the concentration or the product or the charge which flows in this process, the presence and/or concentration of the analyte in the medium is determined. Either or both of the enzyme and the electron mediator are immobilized on the electrode.

45 Claims, 27 Drawing Sheets

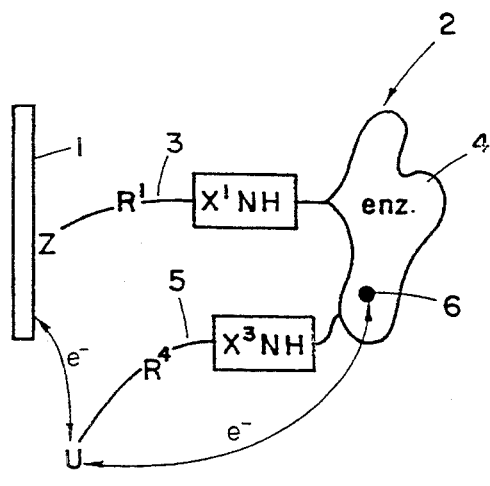
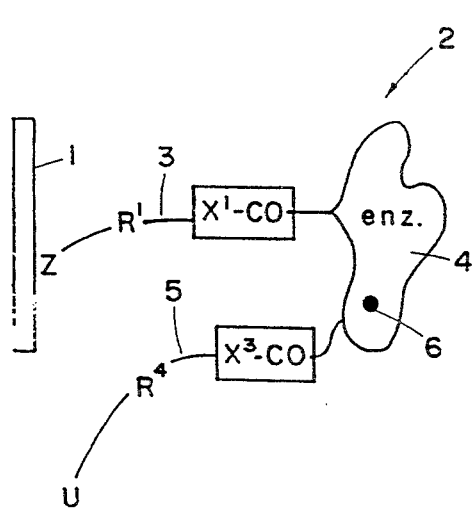
Fig.1(a)          Fig.1(b)
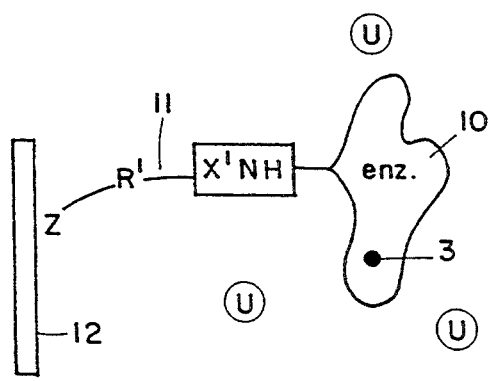
Fig.2
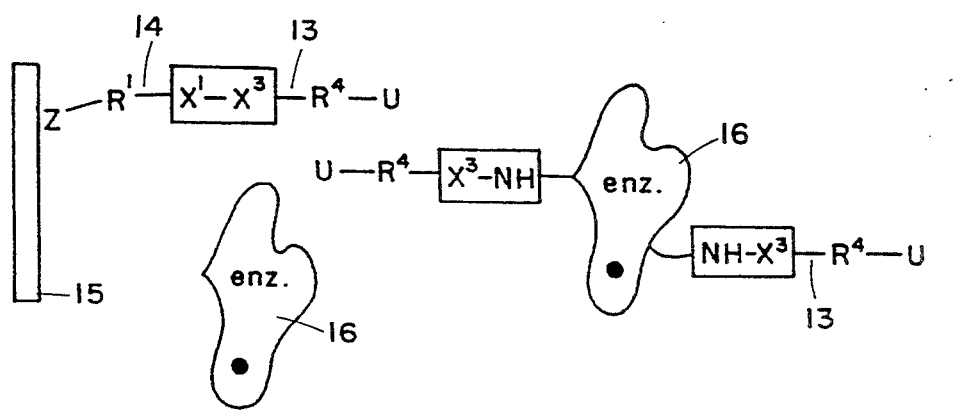
Fig.3

ELECTROBIOCHEMICAL ANALYTICAL METHOD AND ELECTRODES

FIELD OF THE INVENTION

The present invention concerns an analytical method for the determination of the presence and concentration of an analyte in a liquid medium. The method of the present invention is an electrobiochemical method in which the concentration of the analyte in a medium is determined by means of an electrically induced enzymatic redox reaction in which the analyte is converted into a product. The determination of the concentrations of the product or the determination of the charge flow serves as a measure of the analyte's concentration.

The method of the present invention makes use of a novel kind of electrodes, having immobilized thereon either the enzyme molecules, an electro mediator which transfers electrons from the electrode material to the redox center of the enzyme or both.

BACKGROUND OF THE INVENTION AND PRIOR ART

The specificity of enzymes to a specific analyte renders them useful as probes for the detection of the presence of analytes in a liquid medium. A specific class of enzymes which has been proposed for the use in analytical biochemical methods are redox enzymes in which case the detection of the presence and concentration of an analyte in a medium may either be based on the measurement of the flow of charge resulting from the enzymatic redox reaction or on the accumulation of products obtained in the enzymatic redox reaction. In such methods an electrode is used which comprises an electrode material made for example of gold or platinum on which there are immobilized redox enzymes. A redox reaction involves the transfer of electrons from the enzyme to the analyte (in a reduction reaction) or vice versa (in an oxidation reaction) and if there is an electrical communication between the redox center of the enzyme molecules and the electrode material, there is an electrical charge flow which can serve as an indication of the presence of the analyte and the extent of charge flow may serve as an indication of the analyte's concentration. Alternatively, the determination may be based on the measurement of a product of the reaction.

The basic requirement in such electrobiochemical systems is to develop an electrical communication between the enzymes' redox center and the electrode material (Heller, 1990; Wilson et al., 1987). Such electrical communication may be established by immobilization of the redox enzymes in functionalized redox polymers (Degani et al., 1989; Gorton et al., 1990; Foulds et al., 1988) or by chemical modification of proteins with electron transfer mediators (Degani et al., 1988; Heller, 1992). Most of the presently developed electrobiochemical electrodes were utilized in an oxidative pathway. However, it was recently shown that immobilization of enzymes in bipyridinium functionalized polymers (Willner et al., 1990) or functionalization of proteins by bipyridinium components (Willner et al., 1991) gives rise to an electrical communication in photochemical systems which may be used in reductive routes.

It is the object of the present invention to provide an analytical electrobiochemical method for the determination of the presence of an analyte in both reductive and oxidative pathways.

It is furthermore the object of the present invention to provide an electrode for use in the above method.

It is still a further object of the present invention to provide a process for the preparation of such electrodes.

GENERAL DESCRIPTION OF THE INVENTION

In accordance with the present invention it has been found that very efficient electron transfer between the surface of the electrode material of an electrode to redox enzymes by means of an electron mediator group can be achieved if either or both of the enzymes or the electron mediator groups are immobilized on the surface of the electron material by means of groups having sulphur containing moieties which are chemisorbed on said surface, or by linking the electron mediator to the enzyme being immobilized on the electrode material by means of sulphur containing moieties.

The present invention thus provides, in accordance with one of its aspects, an analytical method for determining the presence or concentration of an analyte in a liquid medium by an electrobiochemical enzymatic redox reaction in which electrons are transferred between the surface of an electrode material and a redox enzyme by the mediation of molecular electron mediators whereby the enzyme is capable of catalyzing a redox reaction in which the analyte is converted into a product; said method comprising measuring the concentration of the product obtained in the redox reaction or measuring the flow of charge; the method being characterized in that said electrode material is of a kind which is capable of chemisorption of sulphur containing moieties and that at least one of the components, the enzyme or the electron mediator, is immobilized on the surface of the electrode material by means of a first linking group covalently bound thereto having a sulphur containing moiety chemisorbed to said surface, and the other of said components being either (i) tumbling in the liquid medium surrounding the electrode material, (ii) immobilized on said surface by means of a second linking group having a sulphur containing moiety chemisorbed onto said surface which may be the same or different than said first linking group, or (iii) immobilized on said surface by being covalently bound to said first linking group or to said one of the components.

The present invention also provides in another of its aspects, electrodes for use in the above method, comprising an electrode material of the kind capable of chemisorption of sulphur containing moieties, having immobilized thereon a plurality of complexes each comprising a linking group having a sulphur containing moiety and at least one of a redox enzyme or an electron mediator, all components of the complex being covalently bound to one another.

By a still further aspect of the present invention there is provided an electrobiochemical system for carrying out the above method.

By a yet still further aspect of the present invention there is provided a process for preparing the above electrodes, which process will be outlined further below.

The electrode material may be selected from a large number of conducting or semi-conducting substances having the capability to chemisorb a sulphur containing moiety. Examples of such electrode materials may be gold, silver, platinum or copper and semiconductors such as gallium arsenide.

The linking group may have the following general formula (I):

$$Z-R^1-Q \qquad (I)$$

wherein

Z represents a sulphur containing moiety;

Q is a group $X^1$ or P; $X^1$ is a functional group which is capable of forming a covalent bond with a moiety of said at least one component, i.e. either the enzyme or the electron mediator, as the case may be; P is a protein, a polypeptide or a polymer having a plurality of functional groups $X^2$ having the meaning of $X^1$ above;

$R^1$ represents a connecting group.

Z may for example be a sulphur atom, obtained from a thiol group or a disulphide group, a sulfonate or sulfate groups.

$X^1$ or $X^2$ may for example be a functional group capable of binding to a carboxyl residue of a protein such as an amine group, a carboxyl group capable of binding to amine residues of the protein; an isocyanate or isothiocyanate groups or an acyl group capable of binding to an amine residue of a protein; a halide group capable of binding to hydroxy residues of a protein or a polypeptide, or the polymer P as defined above.

Particular examples of $X^1$ are the groups —$NH_2$; —$CO_2H$; —N=C=S; N=C=O; or an acyl group having the formula —$R^2$—CO—G wherein G may be a group such as OH, halogen, $OR^b$, or a

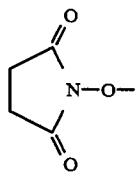

group; $R^a$ and $R^b$ being, independently, a $C_1-C_{12}$ alkyl, alkenyl, alkynyl or a phenyl containing chain, which is optionally substituted, e.g. by halogen.

The functional groups in P may be an amine or a carboxyl group carried on the polypeptide chain, or may be groups carried on a side chain. P may be a polymer or a polypeptide carrying a plurality of functional groups $X^2$ which may be all the same or different and have the same meaning as given above for $X^1$.

Examples of P are polypeptides having free carboxyl or amine groups capable of binding to amine and carboxyl groups in the enzyme molecule, respectively. Particular examples of P are polyamines such as polyethyleneimine and polypeptides rich in glutamate or lysine. P may also comprise functionalized side groups.

$R^1$ may be a covalent bond or may be selected from a very wide variety of suitable groups such as alkylene, alkenylene, alkynylene phenyl containing chains, and many others.

Particular examples of $R^1$ are a chemical bond or a group having the following formulae (IIa), (IIb) or (III):

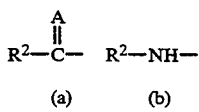

(a) (b)

(II)

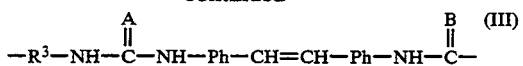

wherein $R^2$ or $R^3$ may be the same or different and represent straight or branch alkylene, alkenylene, alkynylene having 1-16 carbon atoms or represent a covalent bond, A and B may be the same or different and represent O or S, Ph is a phenyl group which is optionally substituted, e.g. by one or more members selected from the group consisting of $SO_3^-$ or alkyl.

The electron mediator is a compound having an electron mediator moiety (represented hereinbelow at times by the letter "U") which is capable of carrying an extra electron and transferring same from the electrode material to the redox center of the enzyme molecule. U should have a redox potential suitable for such an electron transfer.

The electron mediator may either be soluble or may be immobilized on the surface of the electrode material, or may be covalently linked to the enzyme.

Where the enzyme is a reducing enzyme, U may be an optionally substituted viologen such as alkyl viologen—e.g. carboxalkyl bipyridinium having the following formula (IV):

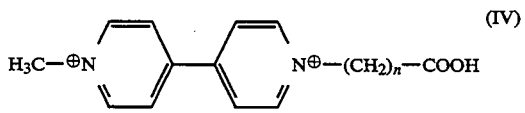

wherein n=1-16.

an optionally substituted pyridinium such as carboxyl substituted pyridinium, e.g. that shown in the following formula (V):

an optionally substituted acridine the substituent being for example carboxyl, e.g. the compound having the following formula (VI):

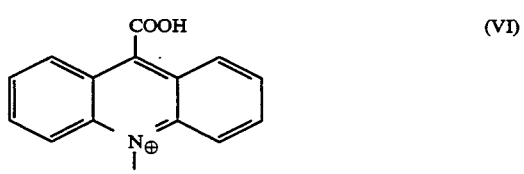

Where the enzyme is an oxidizing enzyme, U may for example be an optionally substituted ferrocene, the substituent being for example alkyl, carboxyl, alkoxycarbonyl, alkylamide or alkylcarboxyl ferrocene such as the compound shown in the following formula (VII):

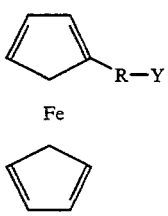

(VII)

wherein Y is an CO₂H or NH₂ group.

Another example for U being an optionally substituted phenothiazine, such as the one shown in the following formula (VIII):

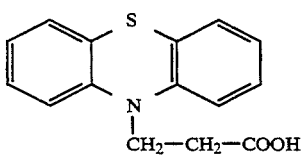

(VIII)

Electron mediators capable of being immobilized on the electrode material have the general formula (IX):

$$U-R^4-X^3 \qquad (IX)$$

wherein U has the meanings given above, $R^4$ and $X^3$ have the meanings of $R^1$ and $X^1$ in formula (I), respectively.

In accordance with one embodiment of the present invention the enzyme molecules are immobilized on the electrode material by means of the linking group and the electron mediator is tumbling in the surrounding solution. In accordance with this embodiment, the electrode material is coated by a plurality of complexes, each comprising a linking group and one or more enzyme molecules.

In accordance with another embodiment of the present invention, the electron mediator groups are immobilized on the electrode material and the enzyme molecules are tumbling in the surrounding solution. In accordance with this embodiment, the electrode material is coated by a plurality of complexes each comprising a linking group and one or more electron mediator groups.

In accordance with a third embodiment of the present invention both the electron mediator groups and the enzymes are immobilized on the electrode material. The electron mediator groups and the enzyme molecules may be in a single molecular complex comprising both the linking group, the electron mediator groups and the enzyme molecule, or may be in separate complexes, one comprising a first linking group and the electron mediator group and another comprising a second linking group which may be the same or different than the first linking group and the enzyme.

Where one of the components, namely either the enzyme or the electron mediator, is freely tumbling in the solution surrounding the electrode and the other component is immobilized, the electrode may comprise a semi-permeable membrane permeable to the tested analyte but impermeable to the tumbling component, enclosing a small volume of solution with the tumbling component between it and the electrode material.

The electrode may comprise a single layer of enzymes all bound directly to a linking group. It may at times be preferred to include several layers of enzyme molecules, in which enzyme molecules of one layer connected to the enzyme molecules of a previous layer by means of bridging groups. Such bridging groups may for example be a group having the following formula (X):

$$W^1-R^6-W^2 \qquad (X)$$

Wherein, $W^1$ and $W^2$ may be the same or different from one another and have the same meanings of $X^1$ in formula (I), and $R^6$ has the meanings of $R^1$ in formula (I).

The bridging group may also be a polymer or a polypeptide having the same meanings as P in formula (I).

Where the electrode comprises a plurality of layers of enzyme molecules, suitably some of the enzyme molecules in the external layer are secondary enzymes intended to decompose interfering agents which may be oxidized or reduced in a non-specific manner, i.e. not by the enzyme, when coming close to the electrode material. Such agents if not decomposed, may seriously affect the results and render them inaccurate. Thus for example, where the enzyme is glucose oxidase, such secondary enzymes may for example be peroxidase to avoid a redox reaction which may be caused by agents such as ascorbate urate or acetaminophen.

In order to prepare electrodes of the present invention, it is possible either first to chemisorb the linking group and then bind the component to be immobilized thereon it, i.e. the enzyme or the electron mediator group. Alternatively, it is possible first to perform the binding between the linking group and said component and then chemisorb the complex on to the electrode material.

Where the electron mediators are immobilized onto the enzyme, it is preferred to immobilize at least some electron mediator groups close to the redox site of the enzyme and for that purpose the enzyme molecule is first unfolded, e.g. by the use of high concentrations of urea, and the electron mediator group is then bound to the unfolded enzyme molecule which is subsequently refolded by decreasing the urea concentration. Suitably, the enzyme molecule is modified by binding to a plurality of electron mediator groups, e.g. 4–12.

BRIEF DESCRIPTION OF THE DRAWINGS

In the following the invention will be described at times with reference to the annexed drawings. In the drawings:

FIG. 1 is a schematic representation of an electrode's surface carrying complexes each comprising a single redox enzyme molecule, an electron mediator group and a linking group. In (a) $X^1$ and $X^3$ are moieties which bind to an amine group of the enzyme molecule; in (b) $X^1$ and $X^3$ are such with bind to a carboxyl group of the enzyme molecule;

FIG. 2 shows a schematic representation of an electrode's surface in accordance with another embodiment in which each complex on the electrode surface comprises an enzyme molecule and a linking group and the electron mediators are tumbling in the surrounding liquid medium;

FIG. 3 is a schematic representation of the surface of an electrode in accordance with another embodiment of the present invention in which each complex chemisorbed on the surface of the electrode material comprises a linking group and an electron mediator group and the enzyme molecules are freely tumbling in the solution and optionally have bound thereto a plurality of electron mediator groups;

DETAILED DESCRIPTION OF THE INVENTION

Figure 4:
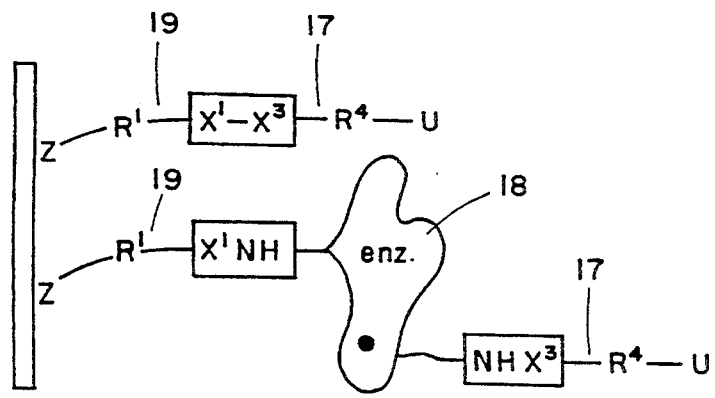
FIG. 4 is a schematic representation of the surface of an electrode in accordance with another embodiment of the present invention in which the electrode carries two types of complexes, one comprising a linking group and an electron mediator group and another comprising a linking group and an enzyme molecule, the enzyme molecule optionally has electron mediator groups bound thereto.

The invention will now be illustrated by several specific embodiments, it being understood that the present invention is not limited thereto. The artisan will no doubt appreciate that the invention can also be carried out by various modifications of its disclosed embodiments as well as by other embodiments and the artisan will have no difficulties of carrying out such other embodiments on the basis of the disclosure in this specification.

Reference is first being made to FIG. 1 which is a schematic representation of the surface of an electrode in accordance with one embodiment of the invention. The surface of a gold electrode 1 is covered by a plurality of complexes 2, each of which consists of a linking group 3, a redox enzyme 4 and an electro mediator group 5. The meaning of $R^1$, $X^1$, $X^3$, $R^4$ and U are as defined above for formula (I).

The nature of the electro mediator moiety U will vary depending on the nature of the redox enzyme. Where the enzyme is an reducing enzyme, suitable electro mediator moieties are for example the groups having the formulae (IV), (V) and (VI) as defined above and where the enzyme is an oxidizing enzyme, a suitable electro mediator moiety is for example a group having the formulae (VII) or (VIII) as defined above.

Examples of enzymes are oxidizing enzymes such as bilirubin oxidase, glucose oxidase, alanine oxidase, xanthene oxidase and lactate oxidase and cholesterol oxidase; reducing enzymes such as glutathione reductase, nitrate reductase, nitrite reductase, and isocitrate dehydrogenase.

In FIG. 1a $X^1$ of the linking group 3 is of a kind which can bind to an amino group in the enzyme. Suitable such $X^1$ groups are for example —N=C=S, —N=C=O or an acyl group having the general formula R—CO—G wherein G is as defined above. $X^1$ in FIG. 1b is of a kind capable of binding to a carboxyl group of the enzyme such as —NH$_2$.

The electron transfer path between the electrode material 1 and the redox center of the enzyme 6 is shown schematically by bidirectional arrows in FIG. 1a, the direction of the electron transfer depending on whether the enzyme is a reductase or an oxidase.

FIG. 2 shows another embodiment of the present invention in which only the enzyme 10 is immobilized by means of the linking group 11 on the surface of the electrode material 12 and the electron mediators U are freely tumbling in the surrounding solution. Transfer of electrons to the redox center of the enzyme is ensured by diffusion of the electron mediators.

In the embodiment shown in FIG. 3, only an electron mediator group 13 is immobilized by means of a linking group 14 on to the surface of the electrode material 15 and the enzyme molecules 16 are tumbling freely in the solution. The enzyme molecules 16 may also, if desired, carry electron mediator groups 13. Electron transfer is ensured by the diffusion of the enzymes which thereby come into contact with the immobilized electron mediator groups.

In the embodiment shown in FIG. 4, both the electron mediator group 17 and the enzyme molecules 18 are immobilized by separate linking groups 19.

Figure 5:
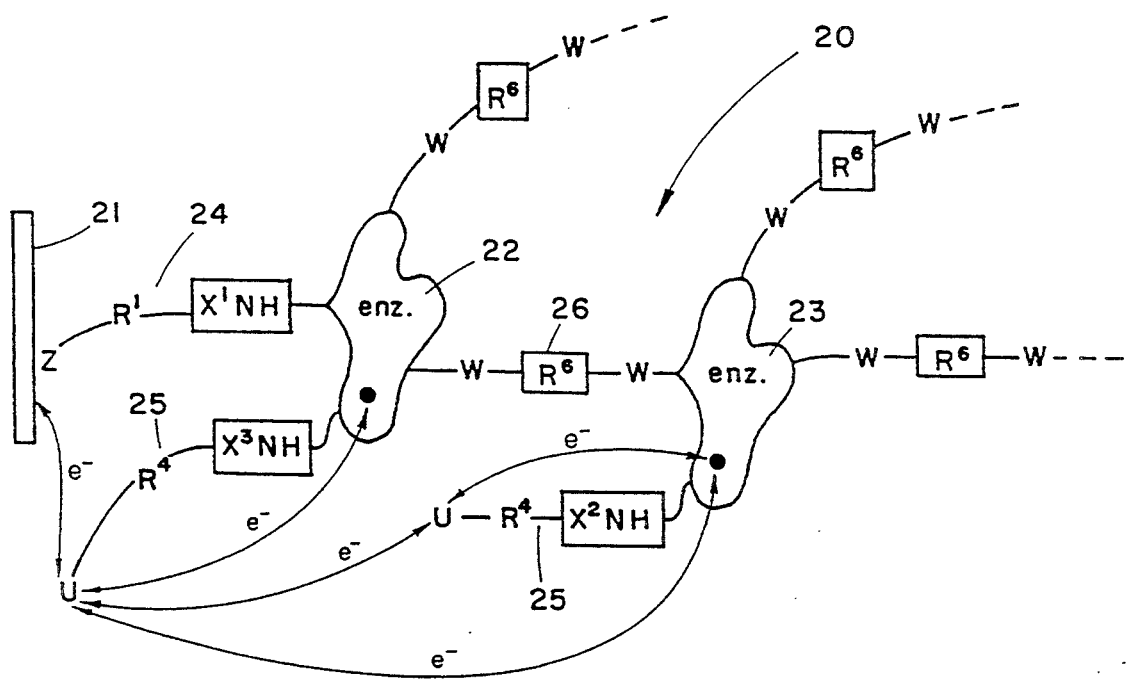
FIG. 5 is a schematic representation of the surface of an electrode in accordance with another embodiment of the present invention carrying complexes each comprising a plurality of layers of redox enzyme molecules, a plurality of electron-mediator groups covalently bound to the enzymes, a linking group chemisorbed on the surface of the electrode material and covalently bound to one of the redox enzyme molecules in the first layer and a plurality of bridging groups linking the redox enzyme molecules of one layer to those of another.

Reference is now being made to FIG. 5 which is a schematic representation of the surface of an electrode in accordance with another embodiment of the invention. Each complex 20 in accordance with this embodiment carried on the surface of the electrode material 21 comprises a plurality of redox enzyme molecules, two of which 22 and 23 are shown. The complex is bound to the electrode material 21 by means of a linking group 24 bound to one of the enzymes 22. The enzymes carry electron mediator groups 25. (As regard the meanings of Z, $R^1$, $X^1$, $X^3$ and $R^4$, see above).

The enzyme molecules are arranged in layers, the enzyme molecules of the first layer being linked by means of linking group 24 to the electrode material and the enzyme molecules of each subsequent layer, being bound to enzyme molecules of a previous layer, by means of bridging groups 26. Bridging groups 26 have the general formula W—$R^6$—W, wherein W and $R^6$ have the same meanings as $X^1$ and $R^1$ in formula (I).

Some of the electron transfer pathways are shown by means of bidirectional arrows, and also here the direction of the electron transfer depends on the nature of the enzyme, i.e. whether the pathway is reductive or oxidative.

Figure 6:
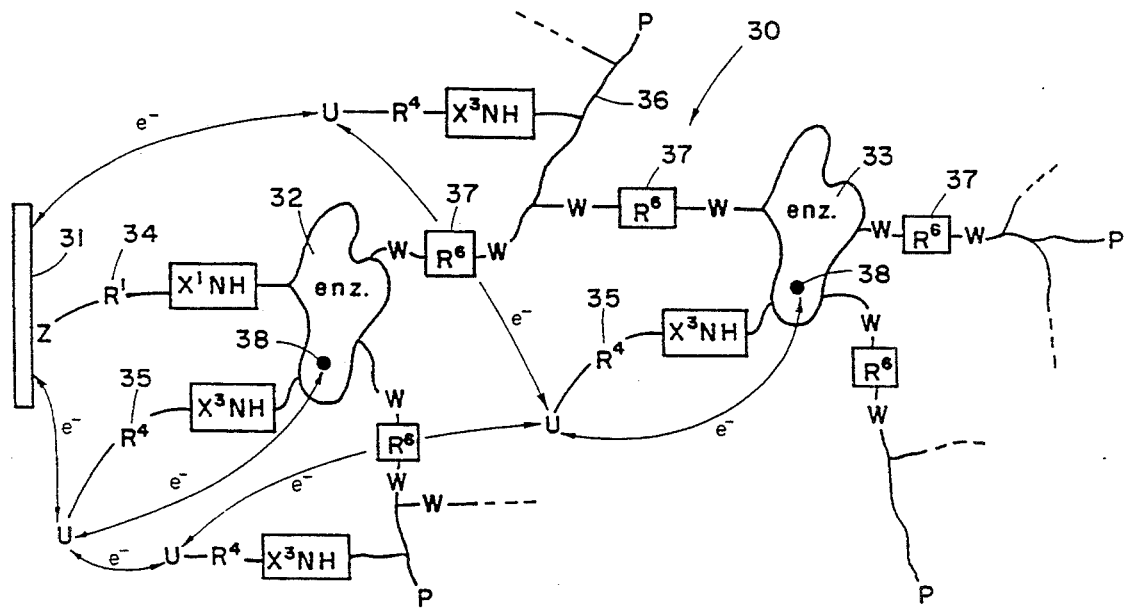
FIG. 6 is a schematic representation of the surface of an electrode in accordance with another embodiment of the present invention carrying complexes each comprising a plurality of redox enzyme molecules in different layers, the enzyme molecules of one layer being linked to those of another by bridging groups comprising a polymeric or a polypeptide chain.

Reference is now being made to FIG. 6 showing a schematic representation of the surface of an electrode in accordance with a further embodiment of the present invention. In this figure, symbols have the same meanings as those which appear already in FIGS. 1 and 2 and the reader is referred to the description in these figures for their explanation. Similarly as in the embodiment shown in FIG. 2, also in this embodiment each complex 30 comprises a plurality of redox enzyme molecules, of which two, 32 and 33 are shown. The complexes are bound to the electrode substrate 31 by means of a linking group 34 covalently bound to enzyme molecule 32. Each of the enzyme molecules has associated therewith electron mediator groups 35, covalently bound thereto.

The enzymes in the complex are linked to one another by bridging groups 36 comprising a polymer or a polypeptide P carrying a plurality of functional groups capable of binding to groups in the protein or to the electro mediator group. For example, where P is a polypeptide rich in lysine, e.g. a polylysine, the amine groups of lysine can readily bind to the carboxylic groups in the enzyme. Where, for example, P is a polypeptide rich in glutamate, e.g. a polyglutamate, the carboxyl groups of glutamate can readily bind to amine groups in the enzyme molecule. Where P is a polypeptide, it carries bi-functional groups 37 having the same nature as the bridging groups 26 in the embodiment shown in FIG. 5.

Bi-directional arrows show some of the complex electron transfer pathways between the electrode material 31 and the redox centers 38 of the enzyme molecules. Here as well, the direction of the electron transfer depends on whether the catalytic pathway is oxidative or reductive.

Figure 7:
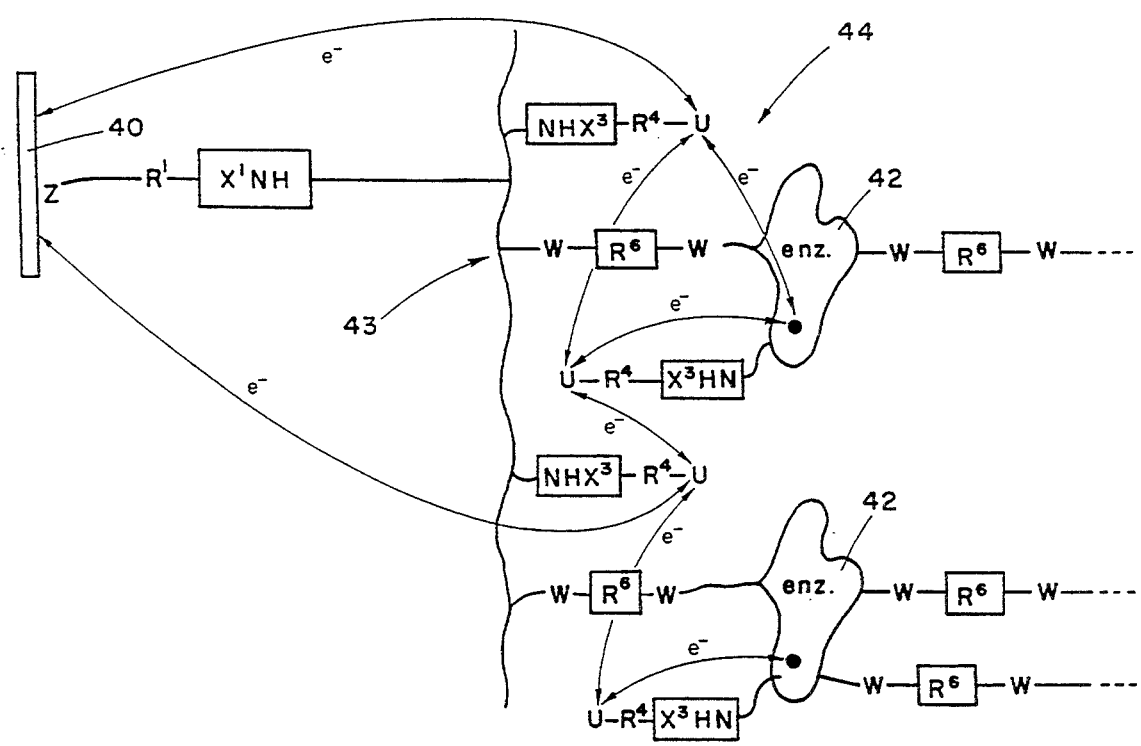
FIG. 7 is a schematic representation of the surface of an electrode in accordance with another embodiment of the present invention carrying complexes each comprising a plurality of redox enzyme molecules all bound to a linking group which comprises a polymeric or a polypeptide chain.

Reference is now being made to FIG. 7 showing yet another embodiment of the present invention. In this figure all like symbols have the same meanings as in previous figures. Complexes 41 of this embodiment comprise a plurality of enzyme molecules 42 linked to electrode material 40 by means of linking group 43. Linking group 43 has a polymer or a polypeptide P which is substantially the same as P in the embodiment shown in FIG. 6.

Some of the complex electron transfer pathways in this electrode are shown also here by means of bi-directional arrows, and again the actual direction being dependent on the nature of their redox pathway.

Also in the embodiment of FIG. 7, additional layers of enzymes can be created.

As pointed out already above, in embodiments in accordance with the present invention where the electrode comprises several layers of enzyme molecules, such as the embodiments shown in FIGS. 5 to 7, the external layers may consist of non redox enzymes intended to disintegrate agents other than the analyte in order to avoid non specific oxidation or reduction, as the case may be, if these agents will come into contact with the electrode material or with the electron mediators. Such agents, if not disintegrated may give rise to non-specific current and thus a decrease in the accuracy of the results.

In accordance with a modification of the embodiments of FIGS. 5 to 7, instead of having an electron mediator group within the complexes or as an addition thereto, it is possible to provide for electron mediation by having electron mediators dissolved in the solution surrounding the electrode. In such a case electron transfer will be ensured by the free diffusion of these compounds in the solution.

Electrodes of the invention are useful for testing for the presence and concentration of specific analytes in a tested sample. In the presence of an analyte in a solution surrounding the electrode, (which solution should also include an electron mediator compound if an electron mediator group is not included as part of the complexes on the electrode), which analyte can be reduced or oxidized by the redox enzyme, as the case may be, and appropriate potential on the electrode is applied, a charge will be transferred to or from the enzyme, respectively, which will provide an indication of the presence of the analyte in the solution. The magnitude of the charge flow will be proportional to its concentration in the solution. Where the enzyme is a reductase enzyme, a negative potential to the electrode should be applied and where the enzyme is an oxidase enzyme, the potential should be positive (in the former case the transfer of electrons is from the electrode substrate to the redox center and vice versa in the latter case).

At times, rather than determining the concentration of the analyte by measuring the charge flow, the concentration will be determined by measuring the concentration of the product of the redox reaction after a certain period of time.

The invention will now be further illustrated by the following examples.

Example 1

Figure 8:
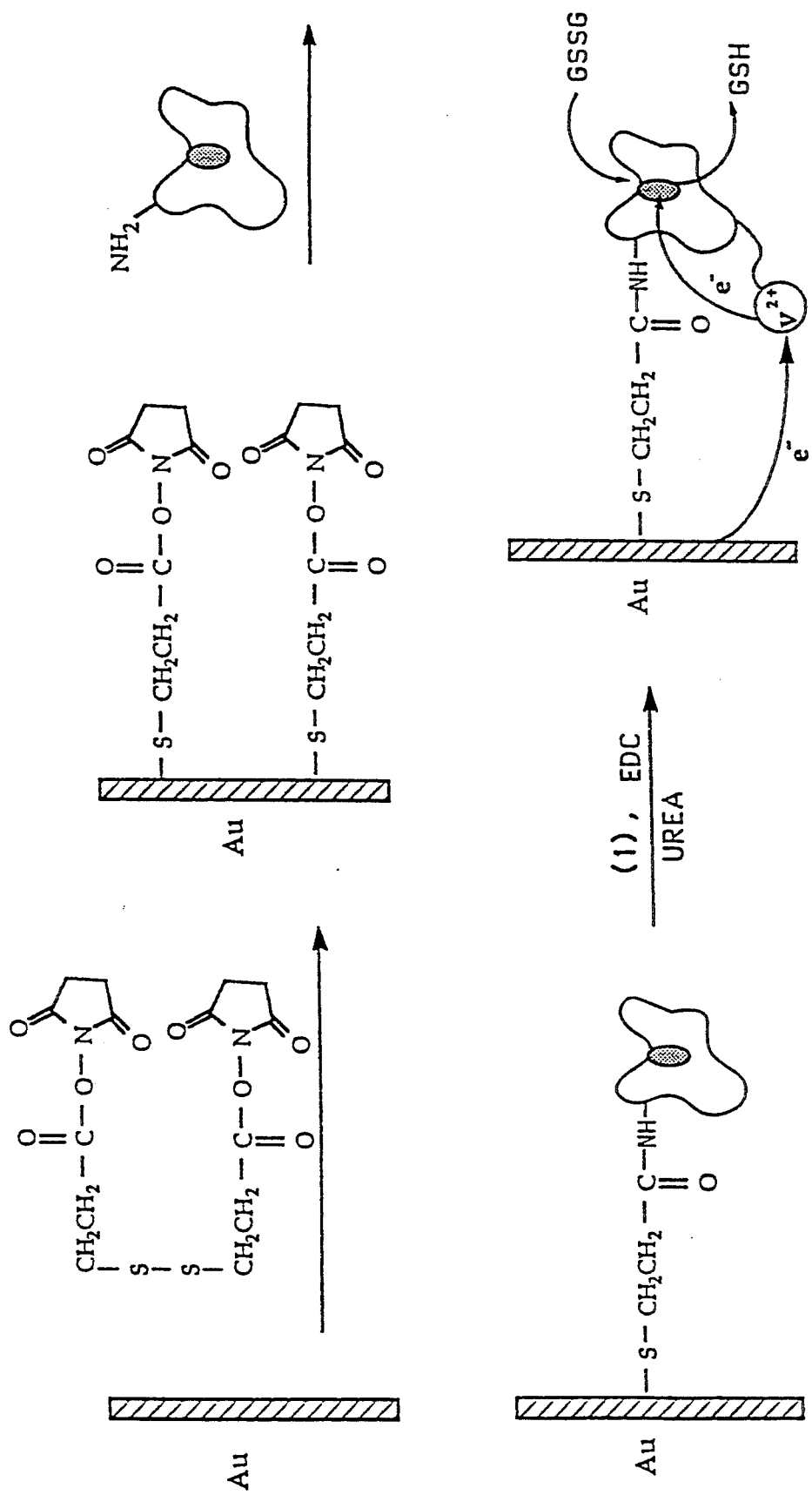
FIG. 8 is a schematic representation of one manner of preparation of an electrode of the kind shown in FIG. 1(a) wherein the enzyme is glutathione reductase, and of the electron-transfer pathways in the obtained complex.

Covalently binding enzyme to an electrode by the use of bifunctional reagents containing sulphur anchor groups in the molecule The procedure described below is depicted schematically in FIGS. 8.

A bare gold (Au) electrode (foil, geometrical area 0.2 $cm^2$) was soaked in concentrated nitric acid for about 10 min., following which the electrode was rinsed thoroughly with water and dimethyl-sulphoxide (DMSO). After such pretreatment the electrode was soaked in DMSO containing $1 \times 10^{-2}$M dithio-bis-(succinimidylpropionate) (DSP, Fluka) for 2 hr, rinsed with DMSO three times and one time with water.

The electrode with bound succinimidyl active ester groups was then incubated overnight at 4° C. in 0.1M phosphate buffer, pH 7.2, containing 100 U/ml glutathione reductase (from bakers yeast, EC 1.6.4.2, Sigma) and rinsed three times with the same buffer to remove non-attached enzyme from the electrode surface.

The same procedure was followed, using however another bifunctional reagent: dimethyl-3,3'-dithiopropionimidate hydrochloride (DTBP, Fluka), having the following formula:

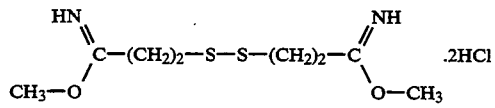

The electrode modification can also be carded out in a water solution rather than DMSO, using water soluble sulphonated bifunctinal reagents such as 3,3'-dithio-bis-(sulfosuccinimidylpropionate) (DTSSP, Pierce), having the following formula:

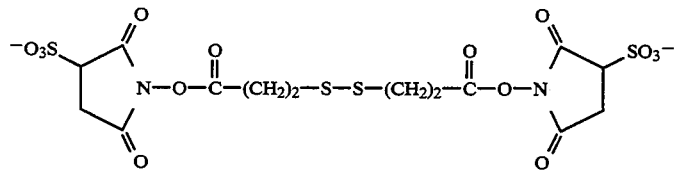

In addition to glutathione reductase, the following other enzymes have also been bound to electrode in the same manner: lipoamide dehydrogenase (from bovine intestinal mucosa, EC 1.8.1.4) and ferredoxin NADP+ reductase (from spinach leaves, EC 1.18.1.2., Sigma) and glucose oxidase.

Figure 9:
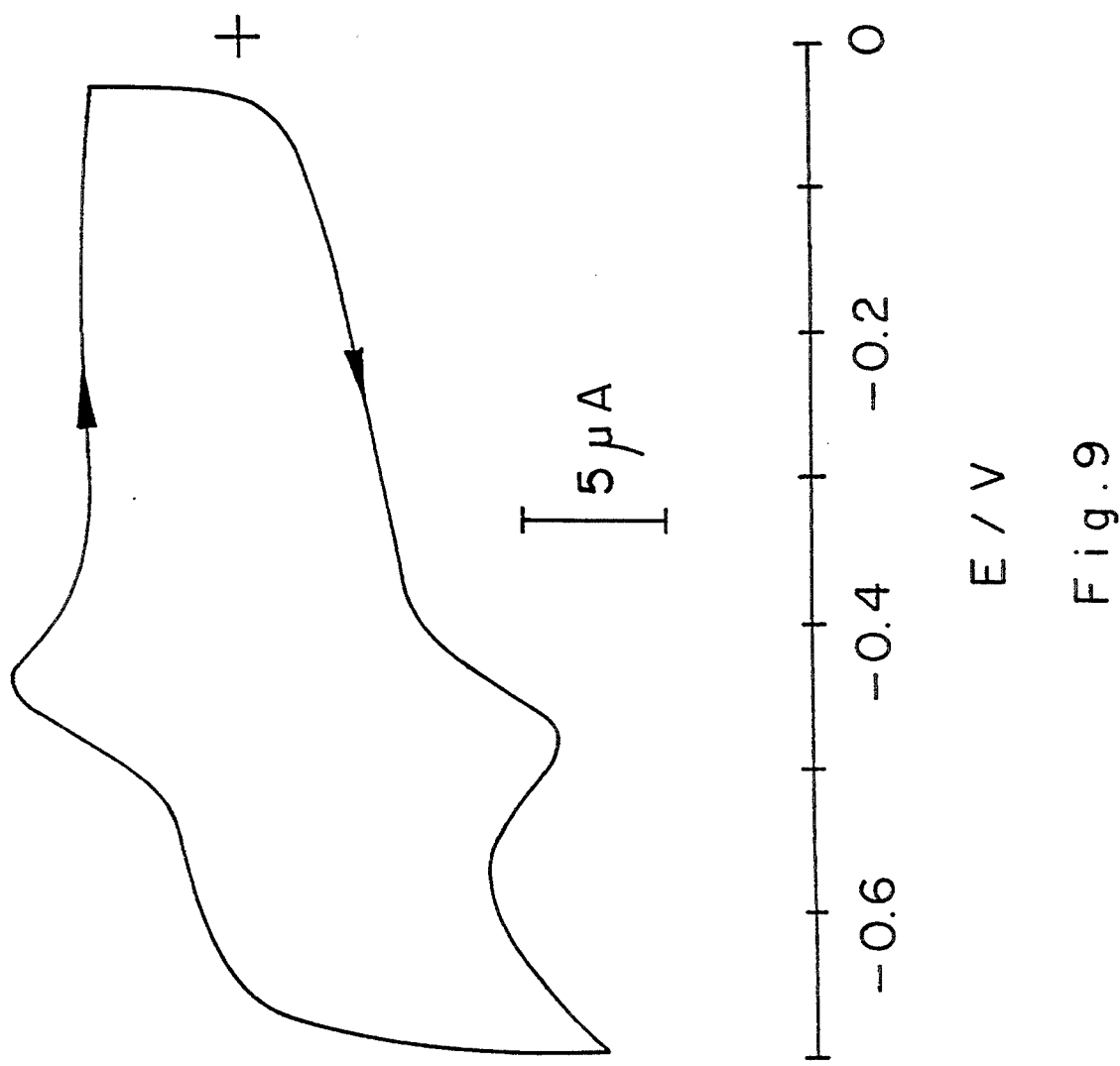
FIG. 9 shows a cyclic voltammogram of a gold electrode modified with DSP and used subsequently for immobilization of amino derivatives of naphthoquinone [potential scan rate: 200 mV/s; background: 0.1M phosphate buffer, pH 7.5]

In order to examine the ability to immobilize amino compounds on electrodes modified by the above mentioned bifunctional reagents, the redox active aminoquinone, 2-chloro-3-(4-aminobutyl)-1,4-naphthoquinone, was bound to the succinimidyl active ester groups. A cyclic voltammogram was obtained against a water background (0.1M phosphate buffer, pH 7.2) and surface concentration of the active group was validated to be about $8 \times 10^{-11}$ mol/$cm^2$ by integration of cathodic or anodic peak (the cyclic voltammogram is shown in FIG. 9).

In order to determine the surface concentration of immobilized enzyme on the electrode surface, glutathione reductase molecules were labelled with $H^3$-iodoacetic acid, and were then immobilized on the electrode. Surface concentration was determined to be about $2\times10^{-11}$ mol/cm$^1$ by measuring the radioactivity of the enzyme modified electrode.

Example 2

Figure 10:
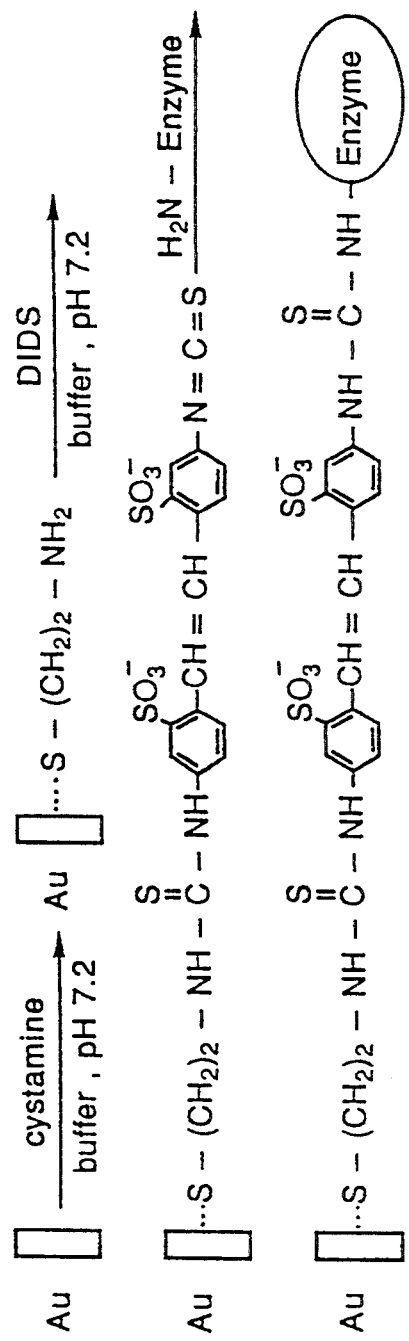
FIG. 10 shows another procedure of immobilization of an enzyme on the surface of a gold electrode.

Preparation of electrode by the use of cystamine or cysteamine for anchoring the complexes The manner of preparation of the electrode as described below, is depicted in FIG. 10.

After pretreatment with nitric acid as described in Example 1, the Au electrode was soaked in 0.1M phosphate buffer, pH 7.2, containing 0.02M cystamine (2,2'-diaminodiethyldisulfide, Fluka) for 2 hr. The electrode was then rinsed repeatedly with distilled water and immersed for 10 min. at 0° C. in the same phosphate buffer containing $1\times10^{-2}$M 4,4'-diisothiocyano stilbene-2,2'-disulfonic acid (DIDS, Pierce).

The modified electrode was rinsed again with water and was incubated for 1 hr at 0° C. in the phosphate buffer containing glutathione reductase, 100 U/ml. The enzyme-modified electrode was then rinsed with the phosphate buffer three times to remove non-immobilized enzyme.

By a similar procedure electrodes were prepared using however cysteamine containing thiol anchor group [$H_2N$—$(CH_2)_2$—$SH$] rather than cystamine, but in this case the soaking of the Au electrode could be decreased to up to about 1 min.

Instead of DIDS, other bifunctional reagents can be used such as bis(succinimidyl)suberate (BS, Pierce), following the same procedure. BS has the following formula:

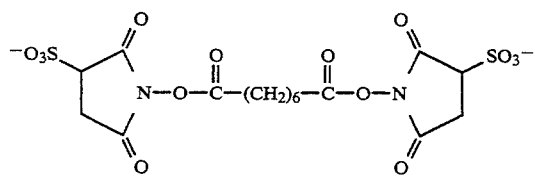

Figure 11:
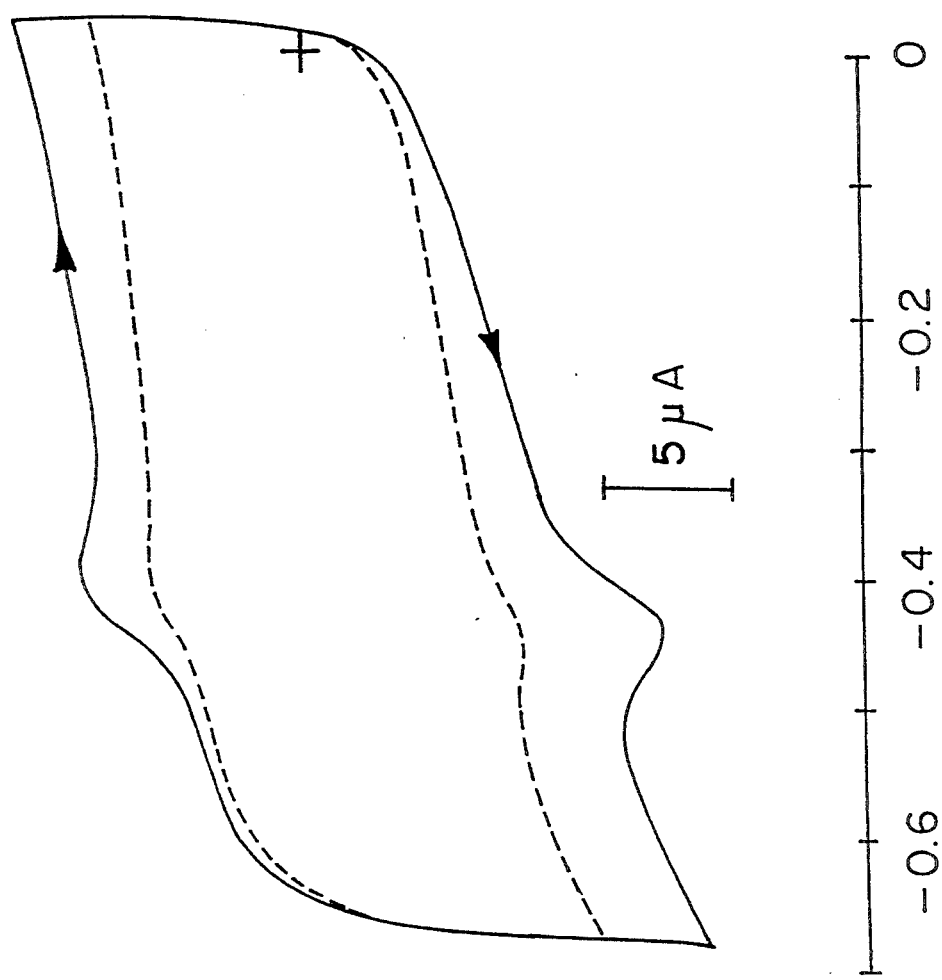
FIG. 11 shows a cyclic voltammogram of a gold electrode modified with cystamine and 2,3-dichloro-1,4-naphthoquinone: quinone immobilization was carried out before (solid line) and after (dashed line) electrode treatment with DIDS for 1 hr [potential scan rate: 200 mV/s; background: 0.1M phosphate buffer, pH 7.5]
Figure 12:
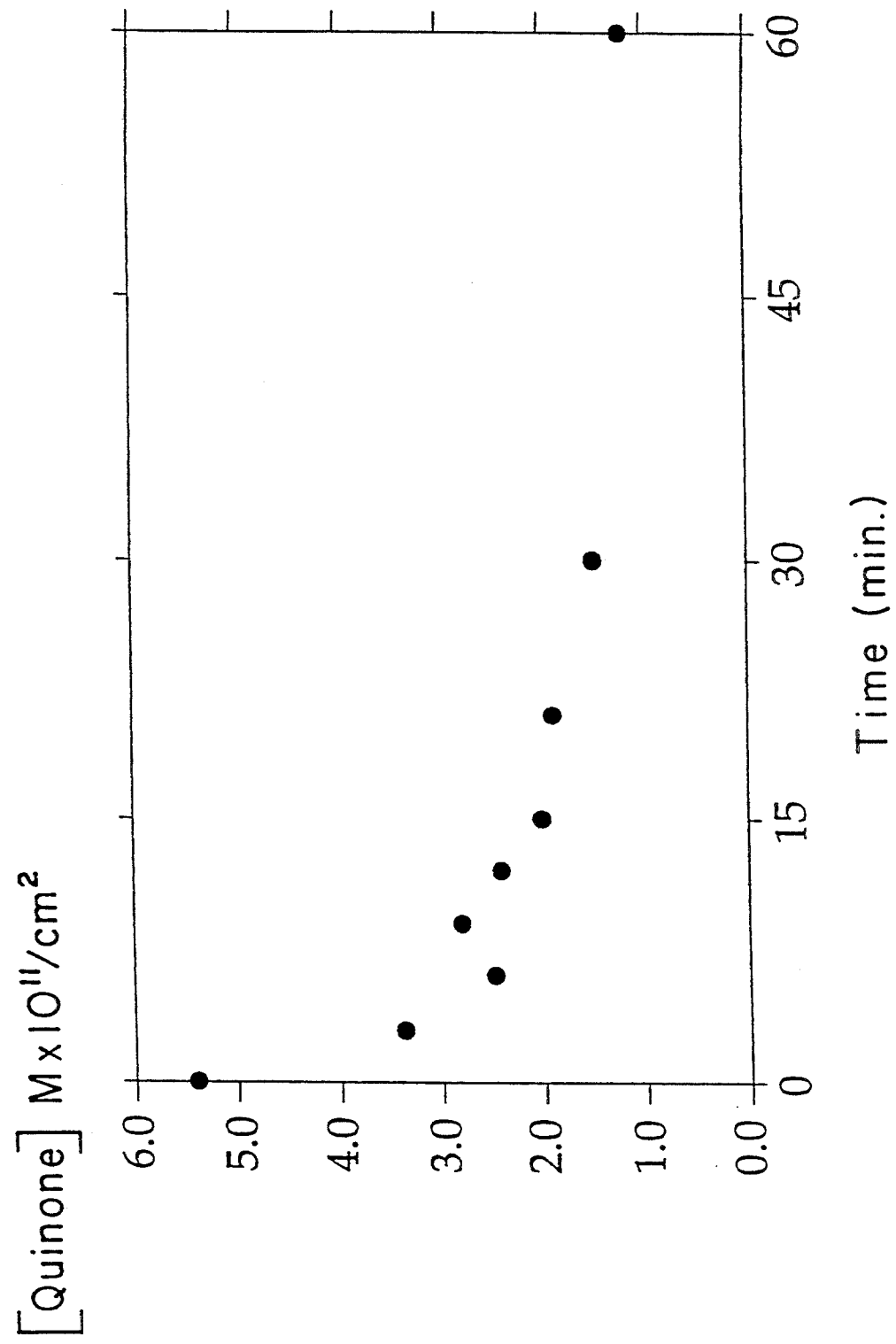
FIG. 12 shows surface concentration of quinone immobilized via amino groups of cystamine versus time of electrode pretreatment with DIDS; the concentrations were calculated by integration of peaks on cyclic voltammograms similar to the one shown in FIG. 11.

In order to determine surface concentration of amino groups just after electrode modification with cystamine (or cysteamine) 2,3-dichloro-1,4-naphthoquinone was bound thereto. By comparison of the surface concentration of amino groups prior to DIDS modification and after such modification, the binding of the quinone in both cases may be compared. FIG. 11 shows a cyclic modified with a cystamine and then modified with the quinone, the second modification being either immediately after the cystamine modification (solid line) or following treatment with DIDS for 1 hr (dashed line). FIG. 12 shows surface concentration of the quinone as a function of the time of the DIDS treatment. As can be seen, after about ten minutes' reaction with DIDS approximately half of the surface amino groups are blocked by the bifunctional regent DIDS.

Figure 13:
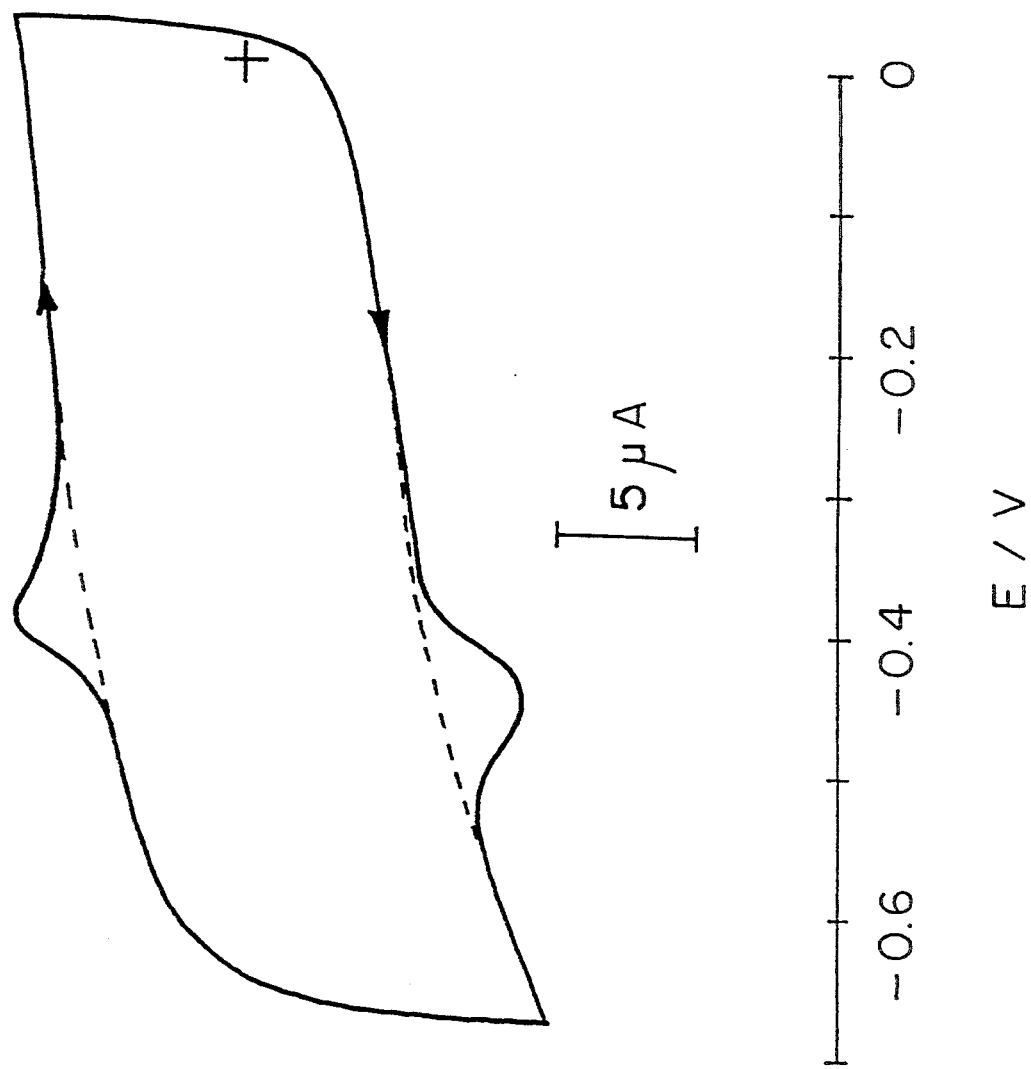
FIG. 13 shows cyclic voltammograms of a gold electrode modified by cystamine, then by DIDS and subsequently by aminoquinone (solid line) and of a control experiment in which prior to reaction with aminoquinone, the DIDS-modified electrode was treated with n-butylamine to deactivate isothiocyano groups on the electrode surface (dashed line)

Another way to estimate surface concentration of DIDS on the electrode surface is covalent immobilization of a quinone with an amino group on the end of a side radical by reaction of the amine group with the active isothiocyano group of DIDS. Cathodic (or anodic) peak integration of cyclic voltammograms of the kind depicted in FIG. 13, gives a measure of the surface concentration of the quinone and this value, while generally in agreement with the value obtained above, shows a slightly smaller concentration, which is believed to originate from deactivation of part of the isothiocyano groups because of their hydrolysis during electrode modification.

Example 3

Activity of the electrode of Example 1

The immobilized enzyme was electrically coupled with the electrode material by dissolving a mobile electron transfer mediator, methylviologen ($MV^{2+}$), $MV^{2+}$ having the following formula:

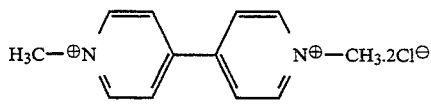

Figure 14:
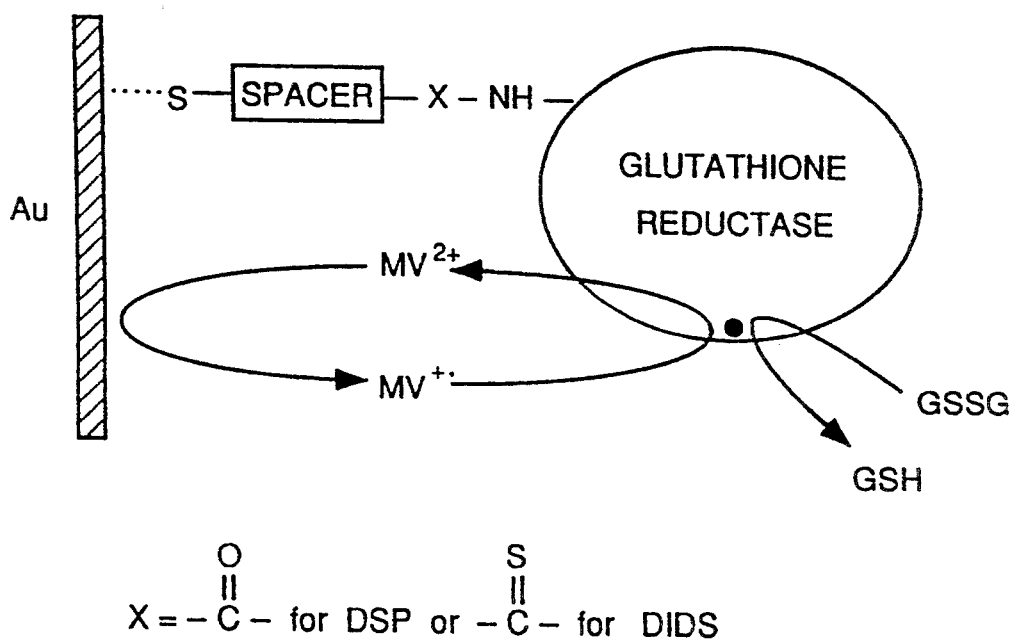
FIG. 14 is a schematic representation of a surface of an electrode modified with DSP and glutathione reductase and the electron transfer from the electrode to the active center of the enzyme being via diffusionally mobile electron transfer mediator ($MV^{2+}$) which results in reduction of the substrate.
Figure 15:
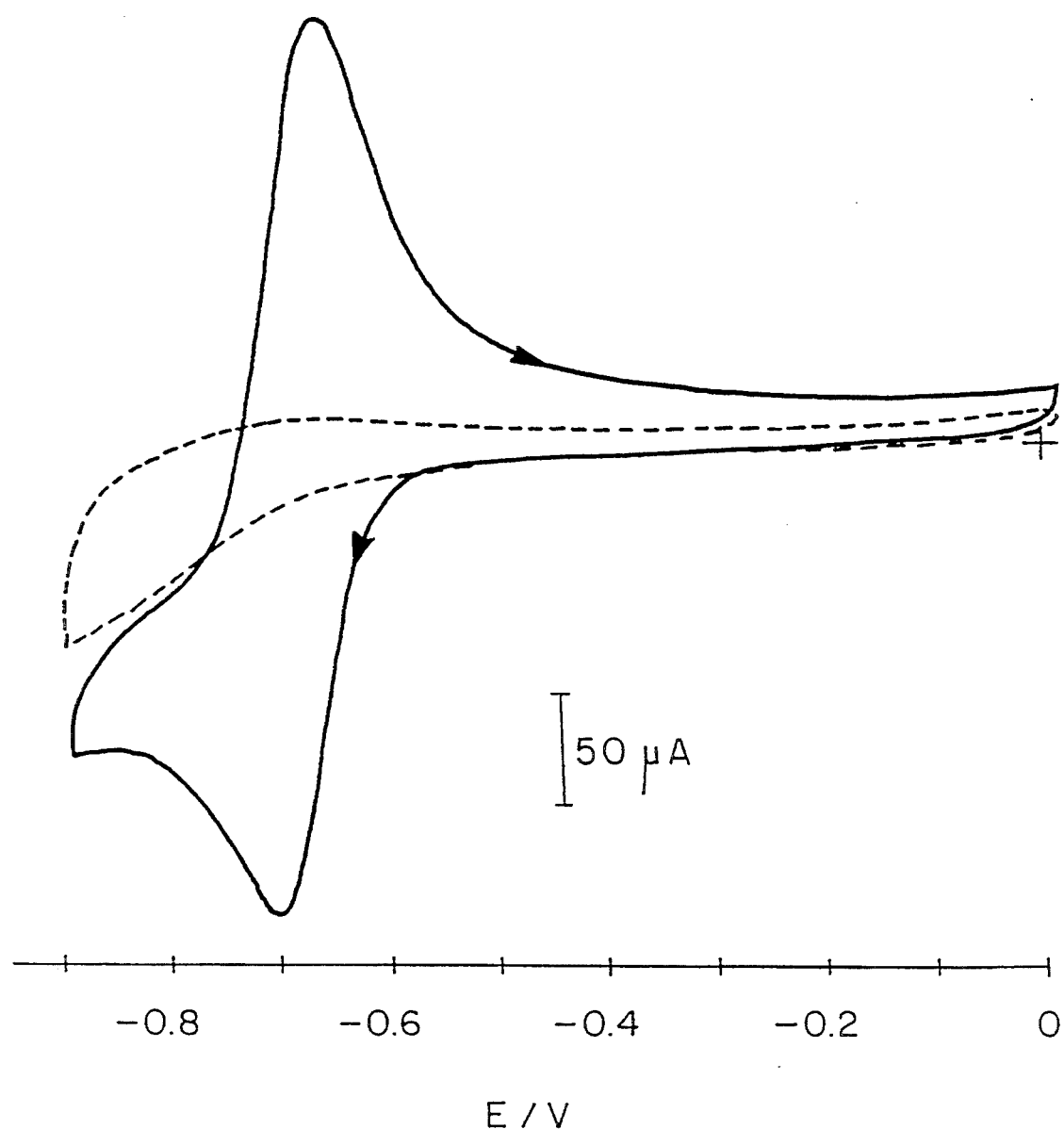
FIG. 15 shows a cyclic voltammogram with a gold electrode modified with glutathione reductase attached to the electrode surface via DSP in the presence of $1 \times 10^{-3}$M methylviologen in the solution, shown schematically in FIG. 14 (solid line) [potential scan rate: 200 mV/sec; background: 0.1M phosphate buffer, pH 7.5 (dashed line)]
Figure 16:
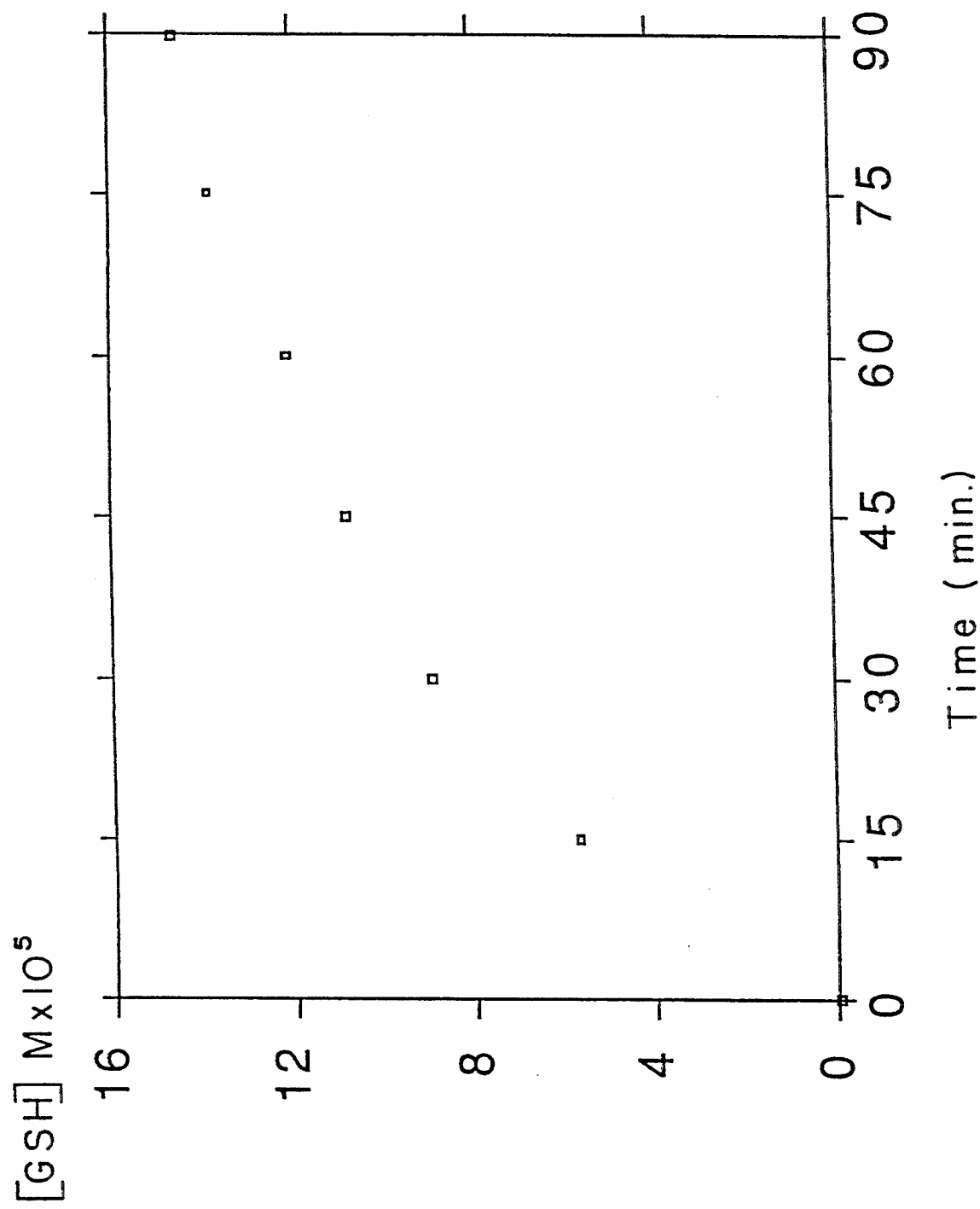
FIG. 16 shows the glutathione reduced form (GSH) accumulation during electrolysis on the electrode modified with DSP and with glutathione reductase and in the presence of $1 \times 10^{-3}$M methylviologen in the solution as a diffusionally immobile electron transfer mediator and $1 \times 10^{-2}$M of GSSG as initial substrate [electrode potential: $-0.7$ V (vs. SCE)]

The electron transfer pathway of this system is shown in FIG. 14. FIG. 15 shows a cyclic voltammogram obtained in a solution containing $1\times10^{-3}$ $MV^{2+}$ and 0.01M glutathione (oxidized form, GSSG) which is a substrate for the enzyme (solid line) and that obtained without $MV^{2+}$ (dashed line). The curve reveals an electrochemically reversible redox process for viologen which indicates that this process is not blocked by the monolayer of complexes which was formed on the surface of the electrode body. Electrolysis in the solution using the enzyme-modified electrode at a constant potential of $-0.7$ V (vs. SCE) results in formation of the reduced form of glutathione, GSH. The accumulation of GSH, which was determined by a spectral analysis, is shown in FIG. 16.

Example 4

Figure 17:
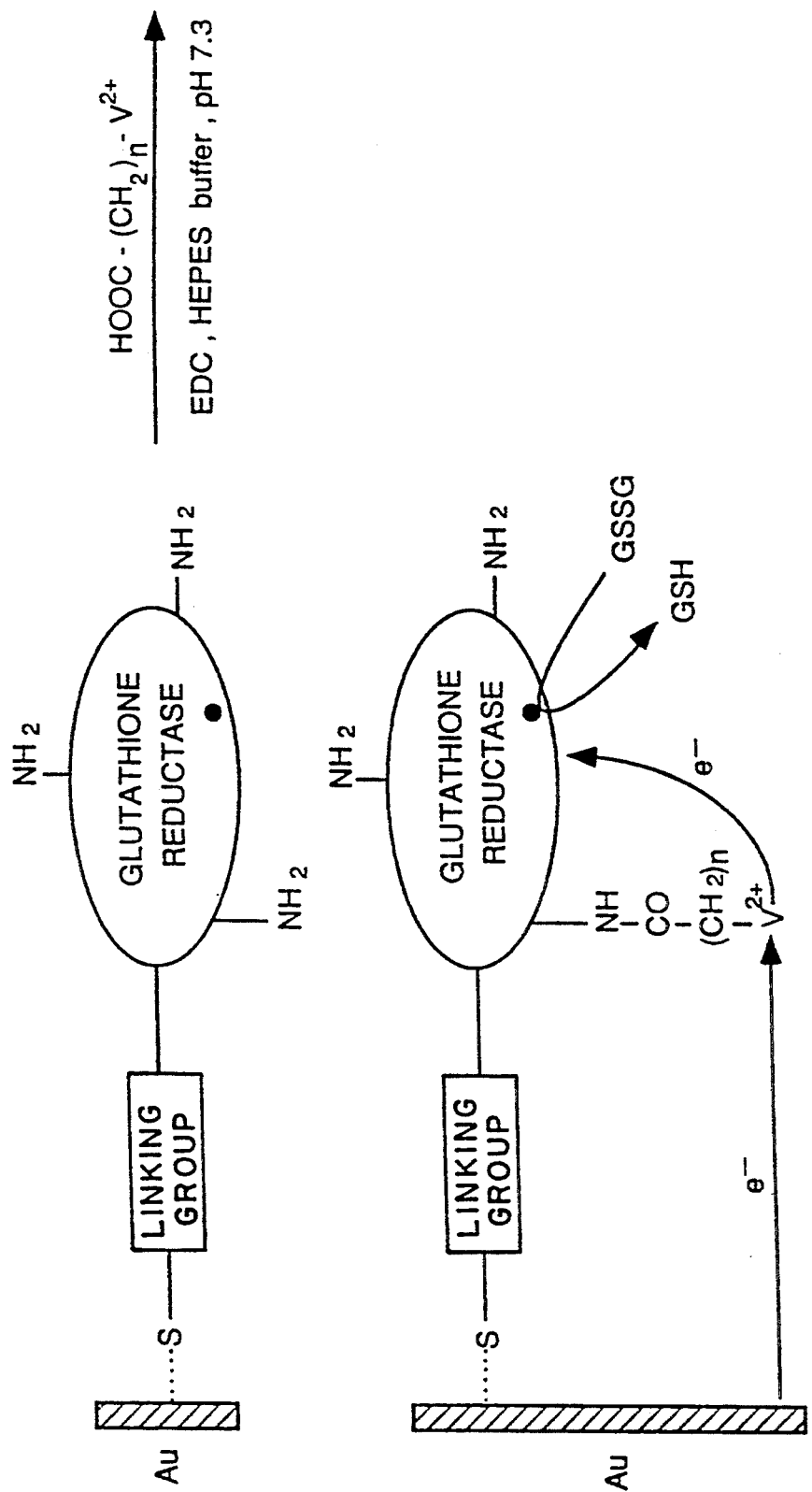
FIG. 17 is a schematic representation of the preparation of a complex on the surface of an electrode consisting of DSP, glutathione reductase and an electron mediator group bound to the enzyme via groups of different chain lengths.

Further modification of electrodes by covalently attaching electron mediator groups to the complexes Electrodes prepared according to Examples 1 or 2 were further modified by carboxy derivatives of viologen with different spacer length and having the following formula:

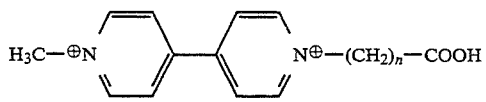

wherein n=1–16. The modification was by means of carbodiimide coupling of their carboxy group with the amino group of a lysine residue in the enzyme molecule. In order to achieve such coupling, the electrodes prepared in accordance with Examples 1 or 2 were immersed overnight at 4° C. in a 0.1M HEPES buffer solution, pH 7.3, containing 0.01M carboxylic acid derivative of viologen, structure IV, 0.01M 1-ethyl-3-(3-dimethylaminopropyl) carbodiimide (EDC) as a coupling reagent and 1.0M urea to open the inner shell lysine residues. After incubation the electrode was rinsed with phosphate buffer, pH 7.3, to remove all non-attached components from the electrode surface. The procedure, and the final electron transfer pathway is shown schematically in FIG. 17.

The electrodes which were obtained were studied by cyclic voltammetry to check for redox transformations of immobilized viologens. Electrochemically reversible reduction was seen having a redox potential $E^0 = -0.58$ V. Similar curves were obtained for all carboxy derivatives of viologen except those having short spacers of 2 methylene groups.

The surface concentration for immobilized viologen was calculated by integration of cathodic (or anodic) peak on the assumption that one electron reduction is characteristic for the first step of viologen redox process and a value of about $1.6 \times 10^{-10}$ mol/cm$^2$ was obtained. Since surface concentration of immobilized protein was estimated to be about $2 \times 10^{-11}$ mol/cm$^2$ (see Example 1) average number of such groups purporting are about 8, namely out of the 39 lysine residues in the glutathione reductase, 8 are modified by these redox groups.

Example 5

Function of electrode prepared according to Example 1 and modified by electron mediator groups according to Example 4

Figure 18:
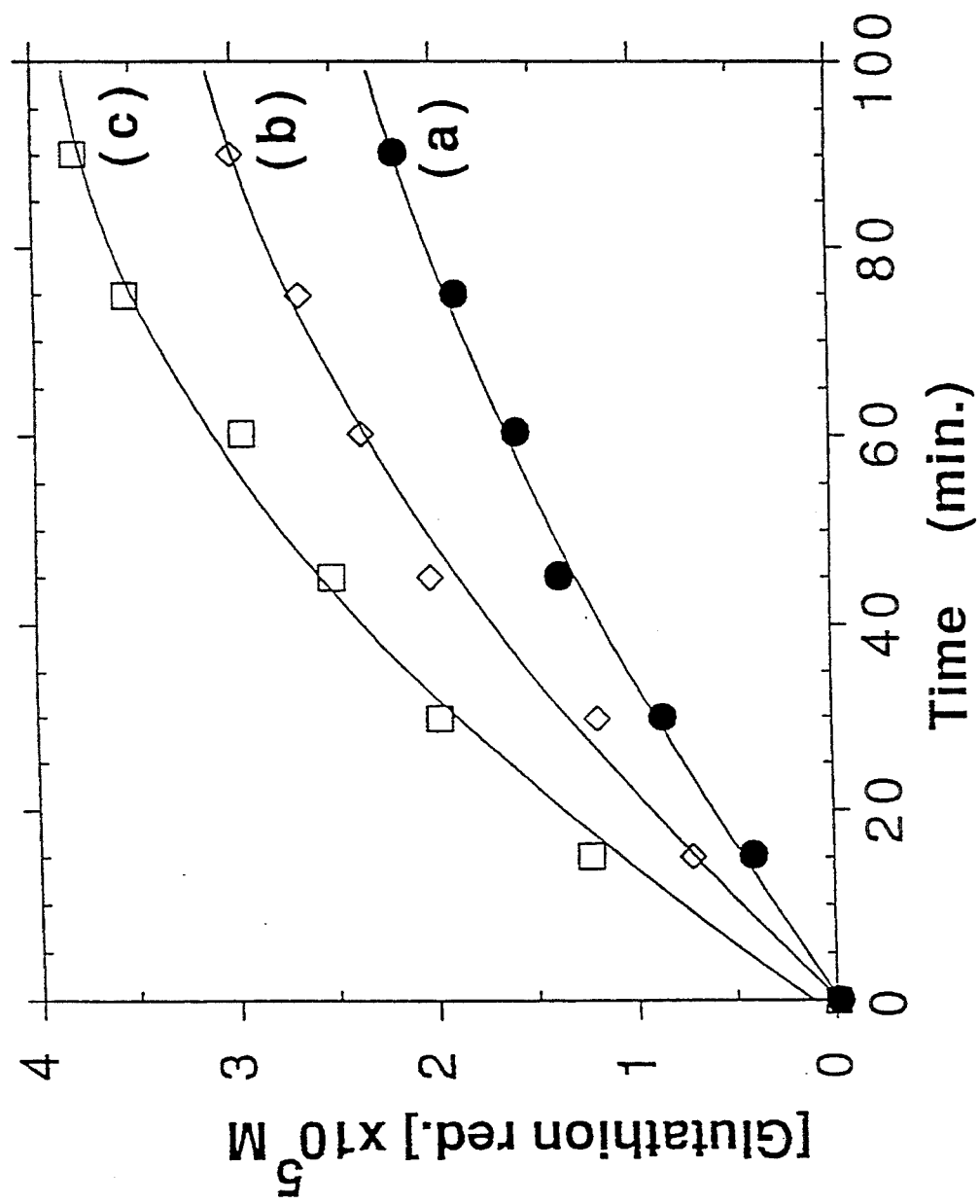
FIG. 18 shows GSH accumulation during electrolysis on an electrode of the kind shown schematically in FIG. 17 with the viologen attached to the enzyme via an alkylene group of different lengths: (a)-$C_2$, (b)-$C_5$ and (c)-$C_{11}$ [electrode potential: $-0.7$ V (rs. SCE); GSSG concentration: $1 \times 10^4$M, pH 7.3 (phosphate buffer)]

Enzyme-modified electrodes prepared according to Example 1 and modified by electron mediator groups according to Example 4 contain redox active components attached directly to the protein globula. An electrode having mediator groups with different spacer lengths (C=2, 5, 11) were used. The electrodes were immersed in a solution containing 0.01M GSSG and 0.1M phosphate buffer, pH 7.2, and a negative potential of $-0.7$ V (vs. SCE) was applied. GSH accumulation was observed by spectral analysis (as in Example 3). The accumulation of GSH as a function of time by using bipyridinium relays having different alkylene chain length linked to the protein, is shown in FIG. 18. As can be seen, there is an improved electrical communication upon lengthening of the spacers which is likely attributable to the enhanced intra protein electron transfer rates as a result of electron-donor distance shortening. Namely, the flexible alkyl "arms" generate a shorter intra protein electron transfer distances between the electron mediator moiety and the active site of the enzyme resulting in enhanced electrical communication.

It was found that the electroenzymatic activity of the electrode strongly depended on the presence of urea during the last step of the electrode preparation: in the absence of urea the electrodes which were obtained had the same electrochemical properties for the immobilized viologens but lacked electrical communication between the immobilized viologens and the active center of the enzymes. For such electrodes, electroenzymatic activity was achieved only in the presence of diffusionally mobile electron transfer mediators.

Example 6

Function of electrodes prepared according to Example 2 and modified by electron transfer mediator according to Example 4

Figure 19:
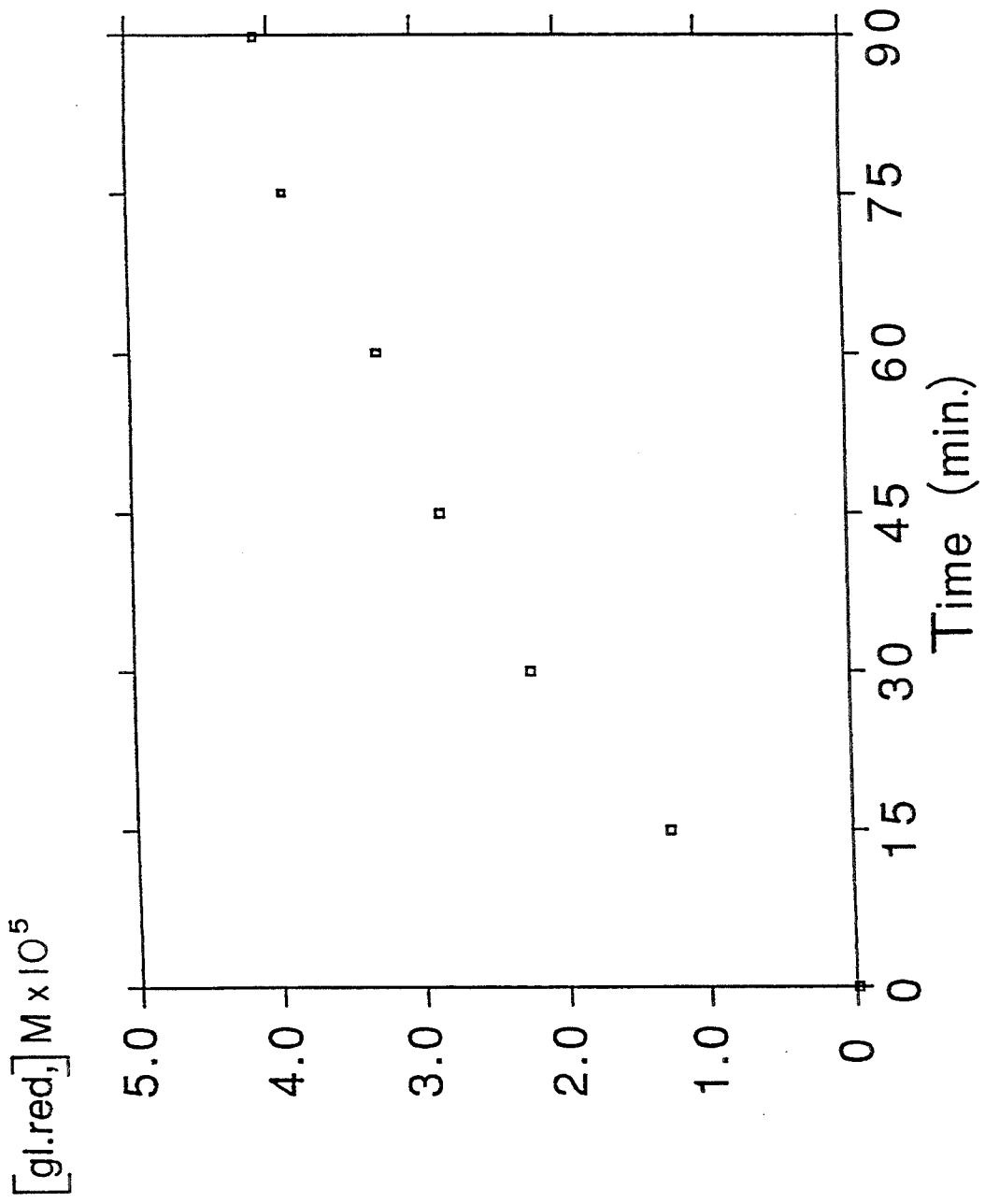
FIG. 19 shows the glutathione reduced form (GSH) accumulation during electrolysis of GSSH using the electrode shown in FIG. 10, with a viologen attached to the enzyme via $C_5$-spacer [electrode potential: $-0.7$ V (vs. SCE); initial concentration of GSSG—$1 \times 10^{-2}$M]

Electron modified electrodes prepared according to Example 2 and modified by electron transfer mediator according to Example 4 contain redox active components attached not only to the protein globula but also to amino groups on the electrode surface many of which are not blocked by DIDS. As was shown in Example 2, electrodes modified by cystamine and treated thereafter by DIDS for 10 min., had approximately 50% of non-blocked amino groups on their surface (see FIG. 12). After modification with carboxy derivative of viologen according to Example 4, this electrode mediator groups were attached both to the electrode surface and to the protein globula. Surface concentration of the immobilized viologen was calculated to be $5 \times 10^{-10}$ mol/cm$^2$ which is slightly higher than the value obtained in Example 4. Rate constant for electron transfer between the electrode and immobilized viologen was calculated as described in Example 4 and very similar values, about 100 s$^{-1}$ was obtained. Electroenzymatic activity of the electrode was studied as described in Example 5 and very similar rate of GSH accumulation was observed as shown in FIG. 19.

Example 7

Immobilization of glucose oxidase on an electrode

Figure 20:
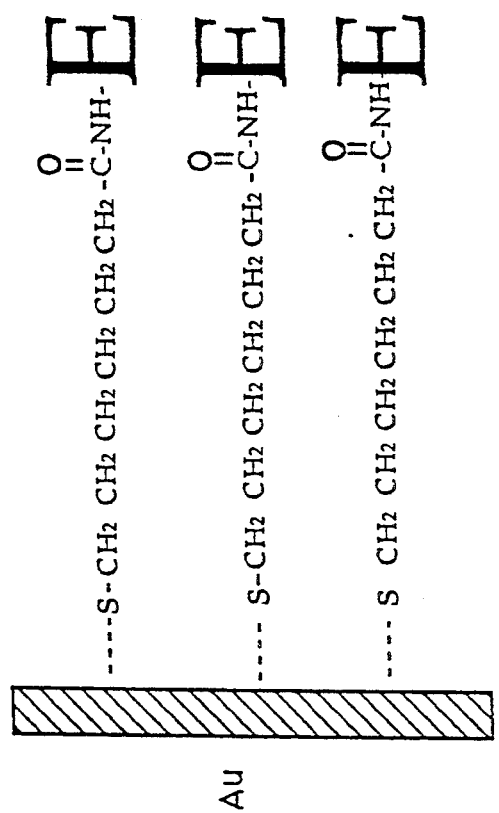
FIG. 20 is a schematic representation of an electrode carrying glucose oxidase enzymes (E) immobilized on the surface of the electrode by means of a 1-thioheptanoic acid linking group.

The gold electrode was incubated in 1-thioheptanoic acid (0.02M) in ethanol overnight, at room temperature. Then the electrode was rinsed five times with ethanol and then again with 7.3 phosphate buffer (0.1M) and was incubated with a solution comprising glucose oxidase 2 mg/ml and with 0.02M of EDC. The surface of the obtained electrode is shown schematically in FIG. 20 (E represents glucose oxidase enzyme).

The cyclic voltammograms (at a scan rate of 2 mV/sec) in the presence of 0.1 mM carboxy derivative of ferrocene (XI) in the

Figure 21:
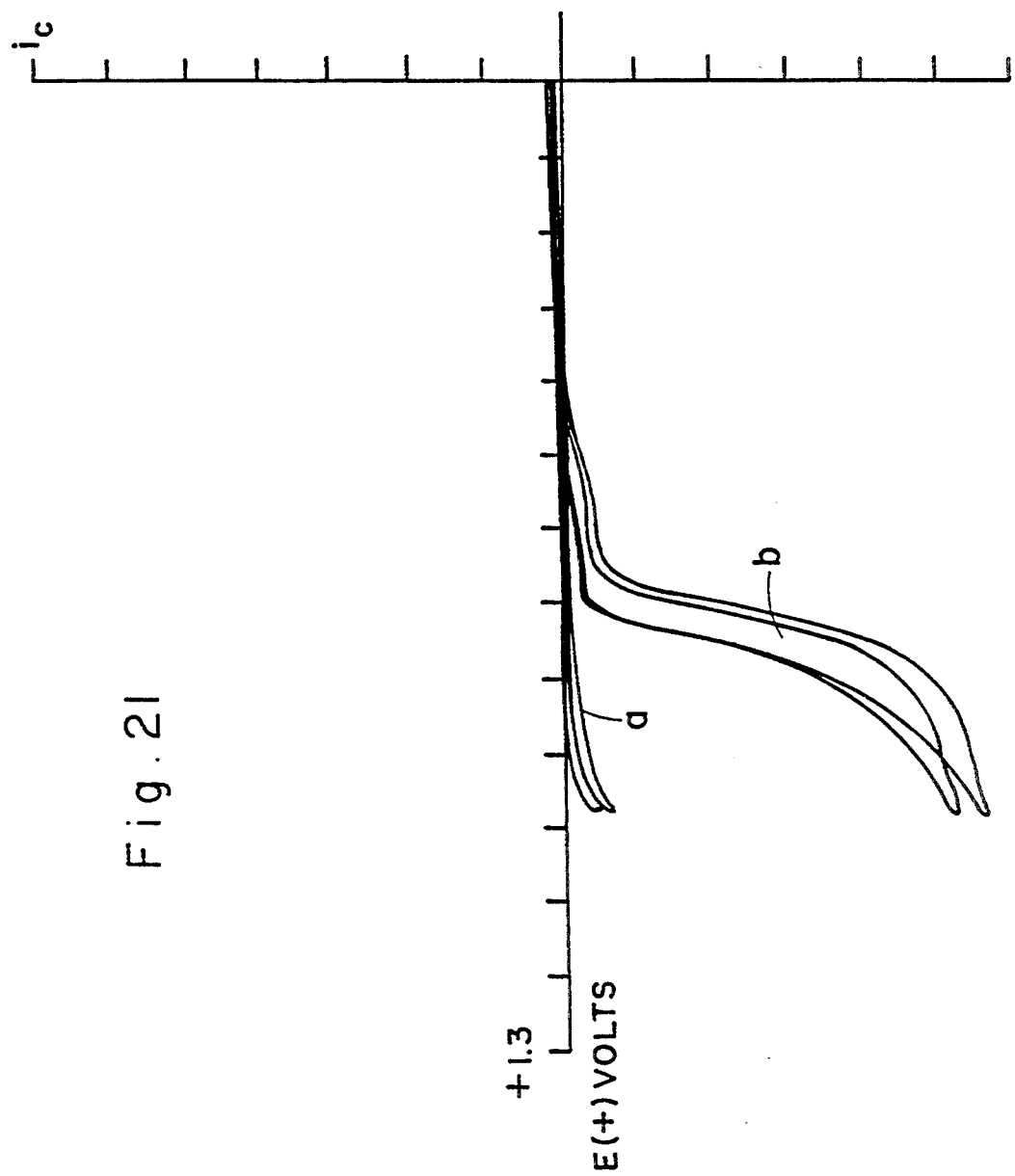
FIG. 21 shows cyclic voltammograms of the electrode of FIG. 20, with $1 \times 10^{-4}$M ferrocene in the solution, the cyclic voltammograms marked (a) were obtained in a solution which did not contain glucose and the cyclic voltammogram marked (b) were obtained in a solution which contained 10 mM glucose [electrode potential: $+0.5$ V (vs. Ag/AgCl)]

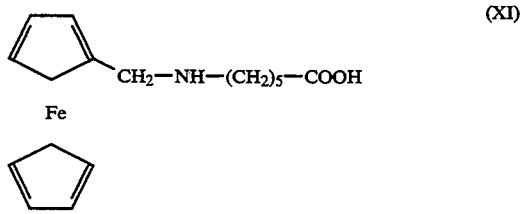

solution, with and without 10 mM glucose are shown in FIG. 21 in which (a) is the cyclic voltammograms without glucose and (b) is the one in the presence of 10 mM glucose.

As can be seen, in the presence of glucose, there is a dramatic increase in the charge flow resulting from the catalytic oxidation of glucose.

Example 8

Use of electrode carrying immobilized ferrocene

Gold electrodes were incubated in a 0.02M cystamine dihydrochloride solution for 2 hr at room temperature. The electrode was rinsed five times with triply distilled water and then two times with 0.1M HEPES buffer pH 7.2. The electrodes were then incubated with 0.02M carboxy derivative of ferrocene (XI) in HEPES buffer in the presence of 0.02M EDC at room temperature overnight.

Figure 22:
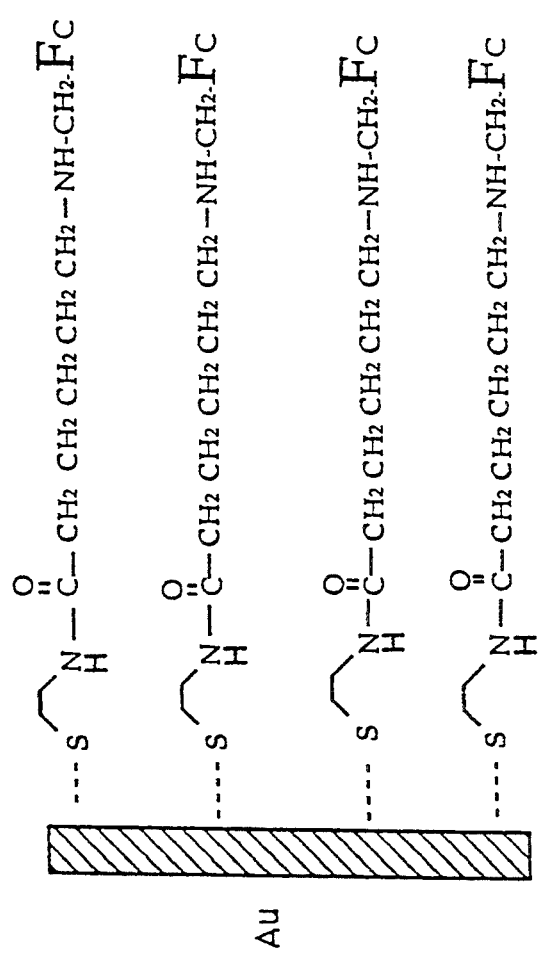
FIG. 22 shows an electrode having ferrocene comprising complexes immobilized thereon.

The surface of the obtained electrode is shown schematically in FIG. 22 (Fc: ferrocene).

Figure 23:
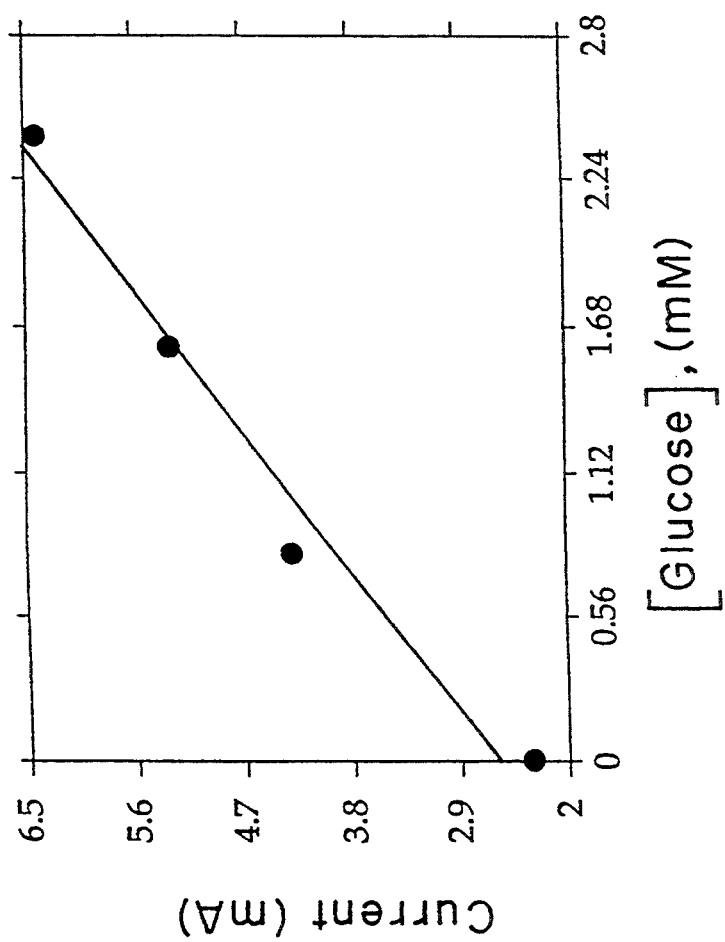
FIG. 23 shows the current obtained at different glucose concentrations with a glucose oxidase enzyme (2 mg/ml) in the solution [electrode potential: $+0.5$ V (vs. Ag/AgCl)]

After this modification the electrode was rinsed five times with the HEPES buffer and checked for the presence of immobilized ferrocene by cyclic voltammetry. 250 units of glucose oxidase were then added to the electrochemical cell and cyclic voltammetry was carried at a scan rate of 2 mV/sec with different concentrations of glucose. The resulting current with the electrode fixed at $+0.5$ V at different glucose concentrations is shown in FIG. 23 and as can be seen there is a linear relationship between the glucose concentration and the measured current.

Example 9

Preparation of electrodes modified with a few layers of the enzyme

Enzyme-modified electrodes prepared according to Example 1 or 2 can be treated again with a bifunctional reagent. The sequence of modification of such an electrode is shown schematically in FIG. 24. After modification of the electrode in accordance with Example 1 or 2 and the binding of the electron mediator group as detailed in Example 4, the electrode was treated for a second time with DIDS for 10 min. at 0° C. After this second modification, a second layer of enzymes was immobilized on the electrode by following the same procedure of Example 4. At times, carboxy derivatives of viologen were attached to the enzyme molecules in the same manner as that described in Example 4. In various experiments, these carboxy derivatives of viologen had various chain length, with the number of carbons in the alkylene varying between 6-11.

After the above-described process, the resulting electrode had two layers of enzymes, and in order to obtain a multi-layer enzyme electrode, this process was repeated for a number or cycles as desired.

Figure 25:
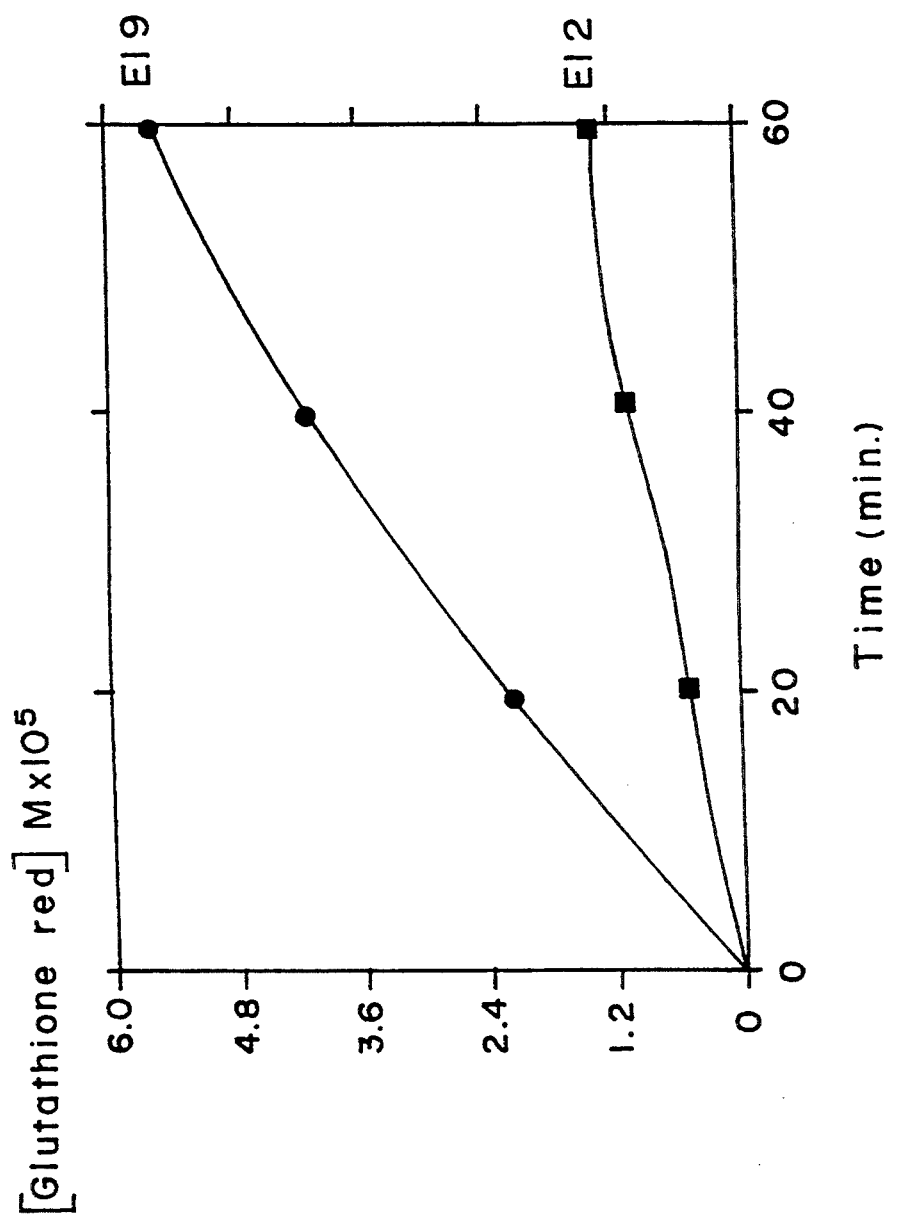
FIG. 25 shows GSH accumulation during electrolysis using an electrode of the kind shown schematically in FIG. 24 (with soluble methyl viologen rather than an immobilized viologen group) with different layers (2 or 9) of enzyme molecules [electrode potential: $+0.5$ V (vs. SCE); initial concentration of GSSG: $1 \times 10^{-2}$M; concentration of solubilized methyl viologen (electron;-transfer mediator): $1 \times 10^{-2}$M]

FIG. 25 shows the accumulation of GSH as a function of time using electrodes which did not comprise immobilized carboxy derivatives of viologen but rather the methyl viologen dissolved in the solutions surrounding the electrode. Electrodes comprising two layers of enzymes (El 2) or nine layers of enzymes (El 9) were used and the concentration of methyl viologen in solution was 10 mM. As can be seen, the rate GSH accumulation in the El 9 electrode is considerably higher than in the El 2 electrode.

Figure 24:
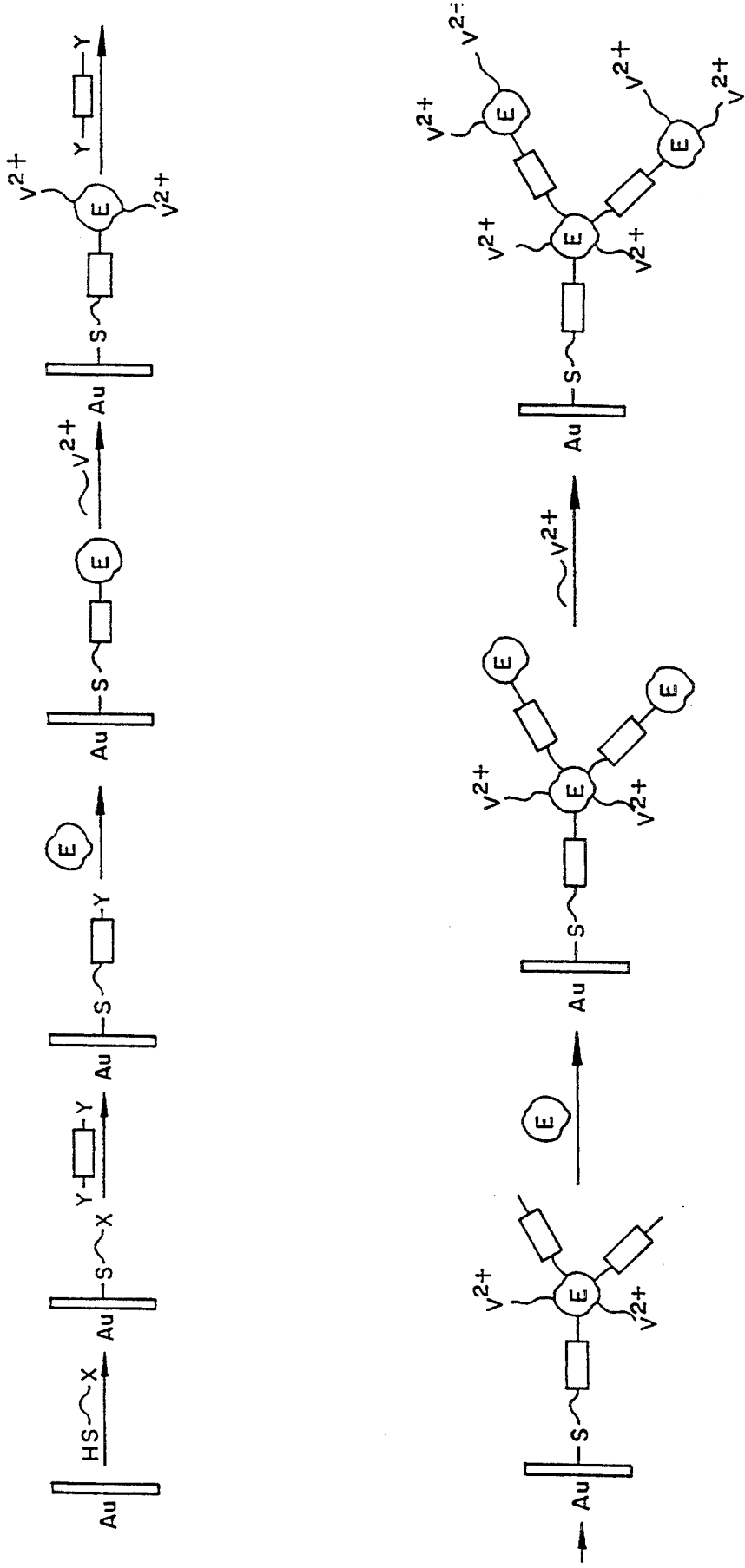
FIG. 24 is a schematic representation of the manner of preparing electrodes having bound thereto complexes of the kind shown in FIG. 5.
Figure 26:
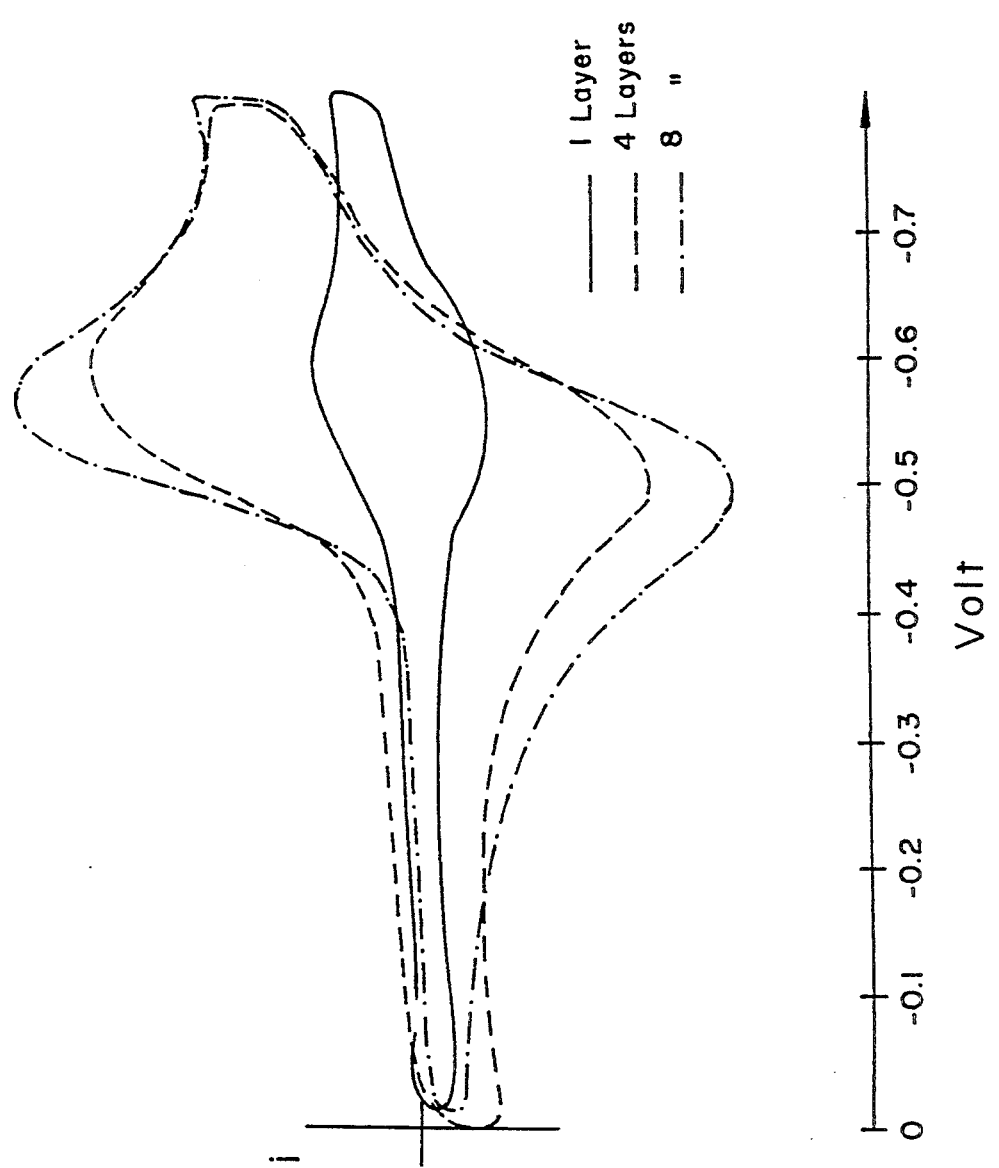
FIG. 26 shows cyclic voltammograms of electrodes of the kind which are prepared in accordance with the procedure shown schematically in FIG. 24, with n=10. Electrodes with one layer, four layers and eight layers of enzymes were tested [potential scan rate: 200 mV/s; background: 0.1M phosphate buffer, pH 7.3]
Figure 27:
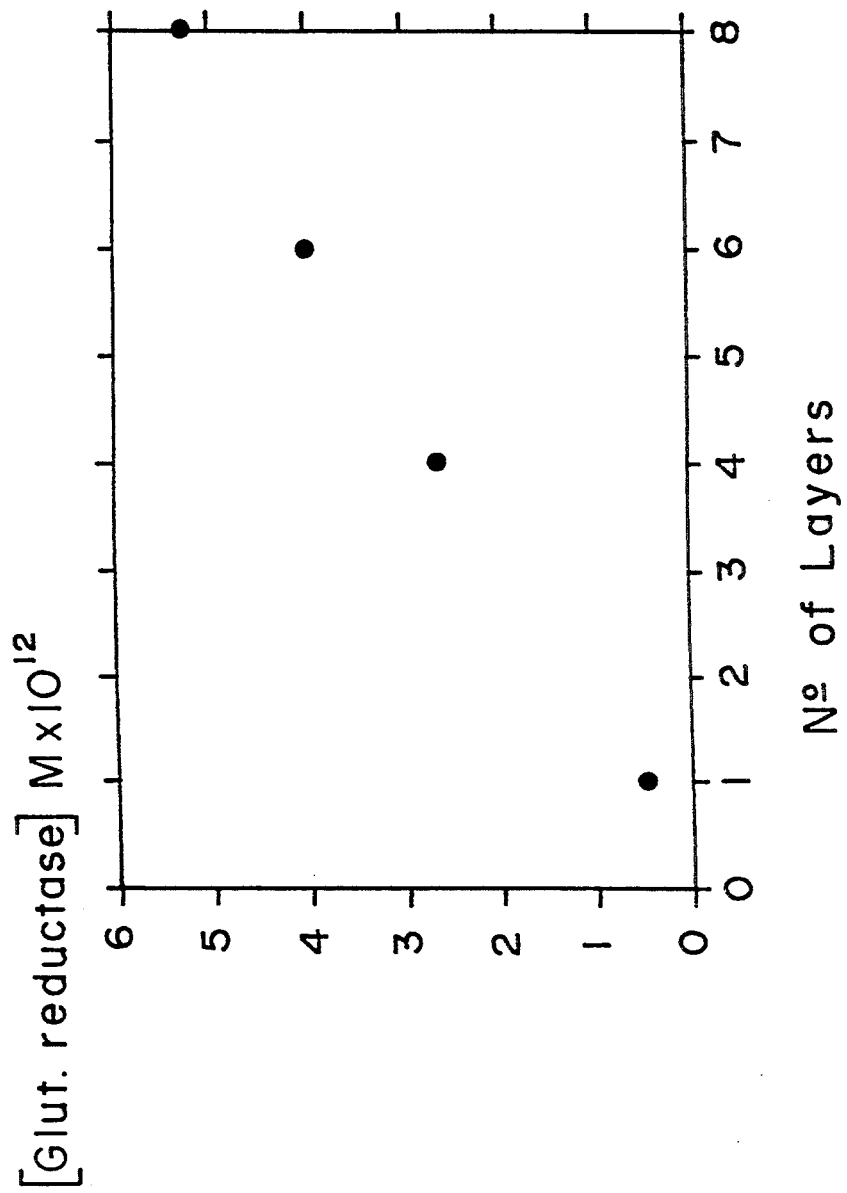
FIG. 27 shows the radioactive labeling of an electrode versus the number of layers of radioactive labeled enzymes on its surface.

Electrodes with several layers of the enzyme glutathione reductase were prepared in accordance with the procedure shown in FIG. 24, including the attachment of carboxy derivatives of viologen (having 10 carbon atoms in the alkylene chain). A cyclic voltammetry experiment was conducted and the results depicted in FIG. 26 show a clear dependence of the electrode electroresponse on the number of enzyme layers.

In another set of experiments the enzymes were radioactively labeled and the labeling versus the number of layers was tested. As can be seen in FIG. 26, a linear relationship between the number of layers and the radioactivity can be seen, indicative of linear increase in the number of enzyme molecules with the increase in the number of layers.

Example 10

Co-immobilization of an enzyme and polymers containing tail redox-active groups

Figure 28:
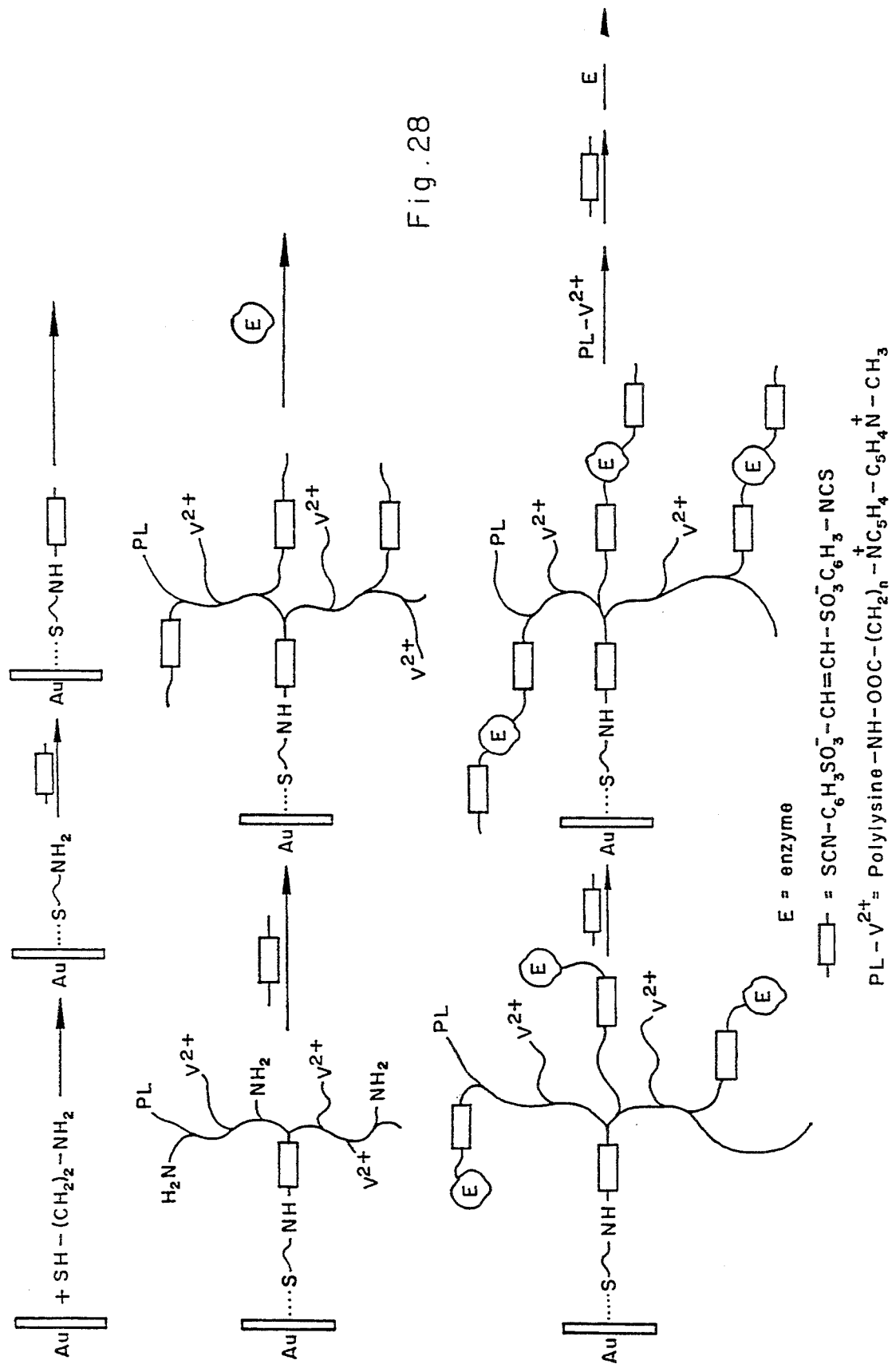
FIG. 28 is a schematic representation of the manner of preparing electrodes of FIG. 7.

The procedure for preparing the electrode of this example is shown schematically in FIG. 28.

An electrode was modified with cystamine and activated with DIDS, as described in Example 2, and then a polylysine chain (PL in FIG. 28) was immobilized on the electrode following a similar procedure to that of the immobilization of the enzymes described in Example 2. The polylysine chains carried bipyridinium groups which were covalently attached to amino groups of the polylysine chain by carbodiimide coupling of the carboxy group of the bipyridinium derivatives and amino groups of the polymer. The loading rate of the bipyridinium groups was made not to be very high so as to leave non-modified amino groups on the polymer.

Following the immobilization of the polymer, the electrode was treated again with DIDS and after rinsing, enzymes were immobilized on the electrodes by covalent binding to the DIDS groups. The procedure of reaction with DIDS and then immobilization of a further layer of polylysine, treatment with DIDS and a further layer of enzyme can be repeated for a number of times to obtain an electrode with a plurality of enzyme layers.

Example 11

Figure 29:
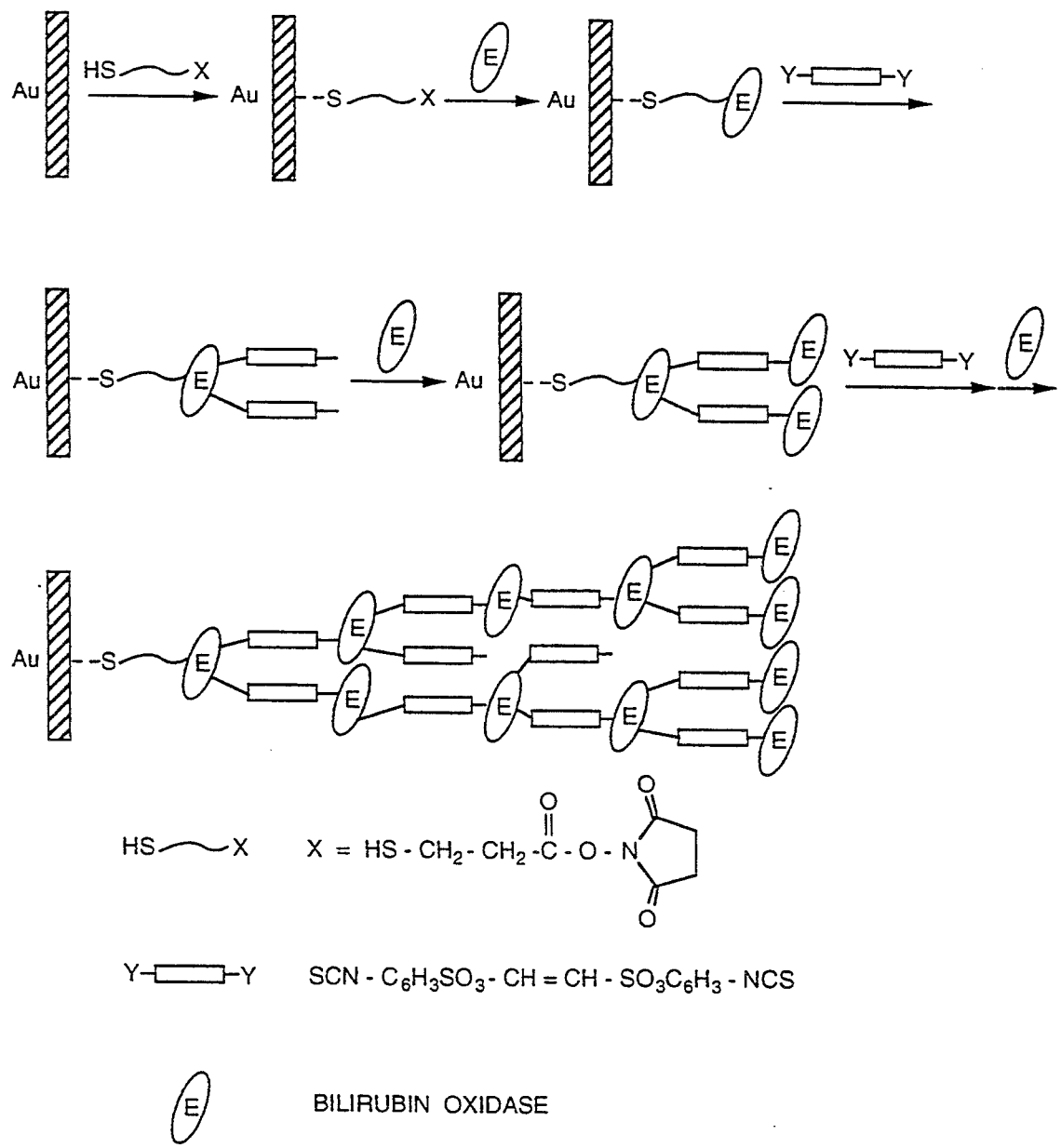
FIG. 29 shows the configuration of the bilirubin oxidase electrode.

Immobilization of bilirubin oxidase on electrode and amperometric determination of bilirubin The procedure of preparing the electrode of this Example is shown schematically in FIG. 29.

A bare gold electrode was successively treated with concentrated $HNO_3$, rinsed with distilled water, rinsed with DMSO, and then modified with $2 \times 10^{-2}$M dithiobis-(succinimidylpropionate) in DMSO, in the manner described in Example 1. The modified electrode was removed from the solution, washed twice with DMSO and once with cold (0° C.) phosphate buffer (0.1M, pH 7.3). The first bilirubin oxidase layer was covalently immobilized to the modified electrode by soaking the electrode overnight at 4° C. in a solution of 100 U of Bilirubin Oxidase in 2.5 ml of the phosphate buffer, and then washing it with cold phosphate buffer. A successive layer of bilirubin oxidase was linked to the base layer by DIDS. The enzyme electrode was dipped in 2.5 ml of cold (0° C.), 0.02M solution of DIDS in phosphate buffer (0.1M, pH 7.3) for 10 minutes. The electrode was then removed from the DIDS solution, washed twice with cold phosphate buffer, and then soaked in the enzyme solution at 0° C. for 30 minutes. This process was repeated until the desired number of layers of bilirubin oxidase was linked to the electrode.

Figure 30:
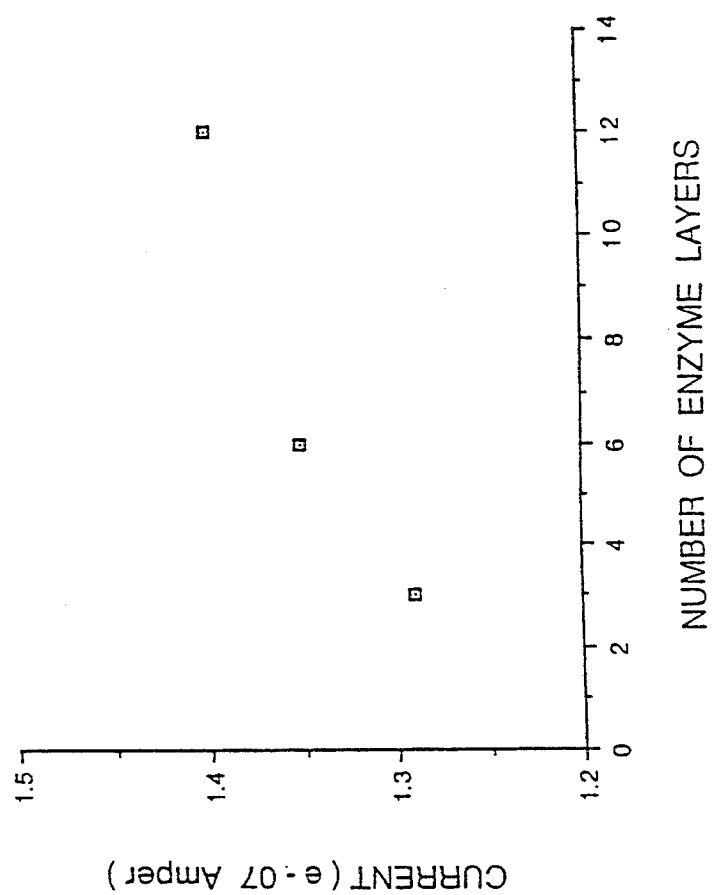
FIG. 30 shows the amperometric response of an electrode comprising of 3, 6 or 12 layers towards a concentration of bilirubin corresponding to $1.7 \times 10^{-4}$M. In this experiment, $5 \times 10^{-4}$M ferrocenecarboxylic acid is used as an electron transfer mediator.
Figure 31:
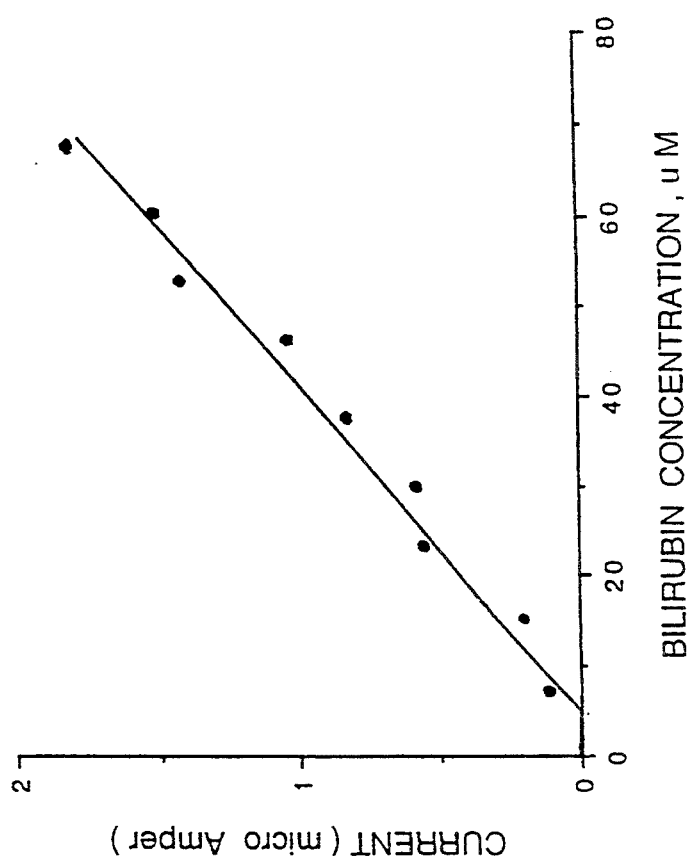
FIG. 31 shows the amperometric response of the electrode toward the concentration of bilirubin. In this experiment an electrode comprising of 8 layers is applied as a sensing electrode.

A catalytic wave with $E^p \approx 0.48$ (vs. $Ag/AgnO_3$) was obtained by cyclic voltammetry with the multiple layer bilirubin oxidase electrode in a solution of bilirubin in TRIS buffer (0.05M pH 8.0) with ferrocene carboxylic acid ($5 \times 10^{-4}$M) as an electron transfer mediator freely tumbling in the solution. The cyclic voltammetry was performed in a glass cell, with the multiple layer bilirubin oxidase electrode as a working electrode, a graphite rod as a counter electrode, and $Ag/AgNO_3$ as a reference electrode. The electrodes remained stable and gave the same catalytic wave for over five weeks of dry storage at 4° C. The anodic peak current increased as more enzyme layers were added as shown in FIG. 30. The amperometric multiple layer bilirubin oxidase electrode had a linear calibration curve, and its anodic peak current was linearly dependent on the bilirubin concentration (FIG. 31).

COMPLETE LIST OF REFERENCES

Willner et al, *Journal of the American Chemical Society*, 1990, 112, pages 6438–6439

Willner and Lapidot, *Journal of the American Chemical Society*, 1991, 113, pages 3625–3626

Foulds et al, *Anal. Chem.* 1988, 60, pages 2473–2478

Heller, *J. Phys. Chem.*, 1992, 96, pages 3579–3587

Gorton et al, *Analytica Chimica Acta.*, 1990, 228, pages 23–30

Degani et al, *Journal of the American Chemical Society*, 1988, 110, pages 2615–2620

Degani et al, *Journal of the American Chemical Society*, 1989, 111, pages 2358–2361

Heller, *Acc. Chem. Res.*, 1990, 23, 128–134

Wilson et al, G. (Eds.) *Biosensors: Fundamental and Applications*, Oxford Univerity Press (New York, 1987)

We claim:

1. An analytical method for determining the presence or concentration of an analyte in a liquid medium comprising the steps of:

selecting an electrobiochemical system, the electrobiochemical system comprising a test electrode which has chemisorbed sulfur containing moieties;

selecting a redox enzyme, the redox enzyme selectively converts the analyte to a product;

binding the redox enzyme to the test electrode;

selecting an electron mediator material which transfers electrons to and from the redox enzyme and test electrode;

introducing a liquid medium with an analyte to the electrobiochemical system;

applying a constant or alternating electric potential to the test electrode so that electrons pass between the redox enzyme and the test electrode allowing the redox enzyme to catalyze the reaction of the analyte; and measuring the concentration of the analyte.

2. A method according to claim 1 wherein the electron mediator material is immobilized on the test electrode.

3. The analytical method of claim 1 wherein the method further includes the step of selecting an electron mediator wherein the electron mediator is selected from the group consisting of viologen, pyridinium, acridine, ferrocene, phenothiazine, substituted pyridinium, substituted acridine, substituted phenothiazine and substituted ferrocene.

4. The analytical method of claim 3 wherein the method further includes the step of selecting an electron mediator from the group consisting of compounds having the following formulae (IV) to (VIII):

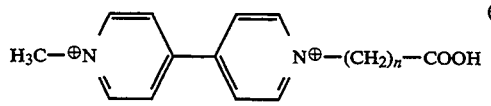
(IV)

wherein n is an integer between 1 and 16;

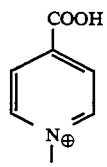
(V)

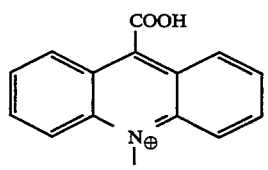
(VI)

-continued

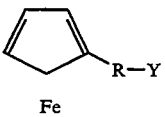
(VII)

wherein Y is $CO_2H$ or $NH_2$

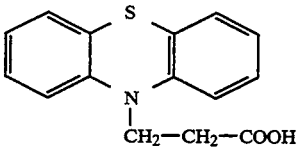
(VIII)

5. The analytical method of claim 1 wherein the method further includes the step of selecting an electron mediator having the general formulae (IX):

$$U-R^4-X^3 \qquad (IX)$$

wherein U is a member selected from the group consisting of viologen, pyridinium, acridine, ferrocene, phenothiazine, substituted viologen, substituted pyridinium, substituted acridine, substituted ferrocene and substituted phenothiazine, $R^4$ is a connecting group, and $X^3$ is a functional group, which forms a covalent bond with a moiety of said at least one component and reacting the electron mediator with the moiety of at least one component to bond the election mediator in vicinity of the redox enzyme.

6. An analytical method according to claim 1 wherein the method further includes the steps of:

selecting an enzyme;
   selecting a bridging group;
   reacting the bridging group with the enzyme; and
   reacting the enzyme with already bound enzyme through bridging groups to form a test electrode.

7. The method of claim 6 wherein the bridging group have the following formula (X):

$$W^1-R^b-W^2 \qquad (X)$$

wherein $W^1$ and $W^2$ may be the same or different from one another and form a covalent bond with a moiety of at least one component and $R^b$ represents a connecting group.

8. The method of claim 6 wherein the bridging group is selected from the group consisting of proteins, polypeptides and polymers, the proteins, polypeptides and polymers having at least one functional group $X^2$ which forms a covalent bond with a moiety of at least one component.

9. The method of claim 6 wherein the enzyme molecules selected for the external layer are non-redox enzymes, the non-redox enzymes catalyzing the reaction of interfering material in the liquid medium.

10. An electrode comprising an electrode material has chemisorbed sulphur containing moieties, the electrode having immobilized thereon a plurality of complexes, each complex comprising a linking group having a sulphur containing moiety and at least one, of a redox enzyme component or a molecular electron mediator component, all components of the complex are covalently bound to one another, the electron mediator transfers electrons between the electrode material and the redox center of the redox enzyme whereby, in the presence of analyte, the enzyme catalyzes a reaction in which the analyte is convened to product.

11. The electrode of claim 10, wherein the linking group has the following general formula (I);

wherein:
Z represents a sulphur containing moiety,
Q represents a group selected from the group consisting of $X^1$ and P wherein $X^1$ is a functional group which forms a covalent bond with a moiety of at least one component and P is selected from the group consisting of proteins, polypeptides and polymers, each having at least one functional group $X^2$ which forms a covalent bond with a moiety of at least one component,
$R^1$ represents a connecting group.

12. An electrode according to claim 11, wherein $X^1$ or $X^2$ is selected from the group consisting of an amine group, a carboxyl group, $-N=C=S, -N=C-O$, an acyl group and

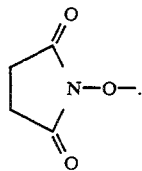

13. An electrode according to claim 12 wherein the acyl group has the formula $-R^a-CO-G$ wherein G is selected from the group consisting of OH, halogen, and $OR^b$ wherein $R^a$ and $R^b$ being independently selected from the group consisting of a $C_1-C_{12}$alkyl chain, $C_1-C_{12}$ alkenyl chain, $C_1-C_{12}$alkynyl chain, a phenyl containing chain, a substituted $C_1-C_{12}$alkyl chain, a substituted $C_1-C_{12}$alkenyl chain, a substituted $C_1-C_{12}$ alkynyl chain and a substituted phenyl containing chain.

14. An electrode according to any one of claims 11 to 13, comprising linking groups of the general formula (I), wherein P is polyamine or a polypeptide with free amine or carboxyl groups.

15. An electrode according to claim 14 wherein P is selected from the group consisting of polylysine, polyglutamate and polyethyleneimine.

16. An electrode according to claim 14, wherein P carries at least one functional group $X^1$ wherein $X^1$ is a functional group which forms a covalent bond with a moiety of at least one component.

17. An electrode according to claim 11, wherein $R^1$ is selected from the group consisting of a covalent bond, alkylene chains, alkenylene chains, alkynylene chains, and phenyl containing chains.

18. An electrode according to claim 17 wherein $R^1$ is selected from the group consisting of a chemical bond, and a group having the following formula (II a), (II b) and (III):
wherein:
$R^2$ and $R^3$ may be the same or different and are selected from the group consisting of a covalent bond and straight or branched alkylene, alkenylenes, alkynylene molecules having 1-12 carbon atoms;

A and B may be the same or different and are selected from the group consisting of oxygen and sulfur;
Ph is a phenyl which is selected from the group consisting of phenyl, alkylphenyl, polyalkylphenyl, phenyl sulfate, alkylphenyl sulfate, polyalkylphenyl sulfate, polyalkylphenyl polysulfate.

19. An electrode according to anyone of claims 10-18, wherein the electron mediators have a mediator moiety U being a member selected from the group consisting of viologen, pyridinium, acridine, ferrocene, phenothiazine, substituted pyridinium, substituted acridine, substituted phenothiazine and substituted ferrocene.

20. An electrode according to claim 19, wherein U is a member selected from the group consisting of compounds having the following formulae (IV) to (VIII):

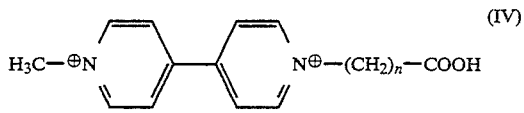

wherein n is an integer between 1 and 16;

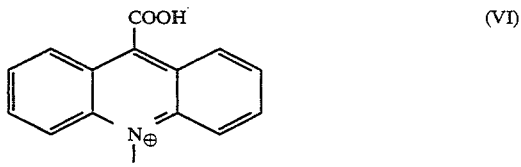

wherein Y is $CO_2H$ or $NH_2$

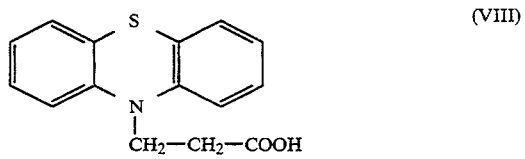

21. An electrode according to any one of claims 10-18 wherein the electron mediator group forms part of said complex and has the general formula (IX):

wherein U is a member selected from the group consisting of viologen, pyridinium, acridine, ferrocene, phenothiazine, substituted viologen, substituted pyridinium, substituted acridine, substituted ferrocene and substituted phenothiazine, $R^4$ is a connecting group, and $X^3$ is a functional group, which forms a covalent bond with a moiety of at least one component.

22. An electrode according to claim 10 comprising several layers of enzymes, enzymes of one layer being linked to enzymes of an adjacent layer by means of bridging groups.

23. An electrode according to claim 22, wherein the bridging groups have the following formula (X):

$$W^1-R^6-W^2 \qquad (X)$$

wherein $W^1$ and $W^2$ may be the same of different from one another and forms a covalent bond with a moiety of at least one component and $R^6$ represents a connecting group.

24. An electrode according to claim 22, wherein the bridging group is selected from the group consisting of proteins, polypeptides and polymers, the proteins, polypeptides and polymers having at least one functional group $X^2$ which forms a covalent bond with a moiety of at least one component.

25. An electrode according to any one of claims 22 to 24 wherein the enzyme molecules in the external layer are non-redox enzymes which catalyst the reaction of agents other than the analyte.

26. A process for preparing an electrode comprising the steps:
    selecting a sulfur chemisorption electrode material;
    selecting a complex comprising a linking group having a sulphur containing moiety, chemisorption of the sulfur containing moiety onto the electrode material;
    selecting at least one of a redox enzyme and an electron mediator and reacting at least one of the redox enzyme and an electron mediator with the chemisorbed linking group.

27. A process for preparing an electrode comprising the steps:
    selecting a sulfur chemisorption electrode material,
    selecting a sulfur containing linking group;
    selecting at least one of a redox enzyme and an electron mediator;
    reacting the selected linking group with at least one of the selected redox enzymes and electron mediators to form a complex; and
    reacting the complex with the electrode material to form the electrode.

28. A process according to claims 26 or 27, further comprising:
    (a) unfolding the enzyme molecule;
    (b) binding electron mediator groups to the unfolded enzyme molecule;
    (c) refolding the enzyme.

29. The analytical method of claim 1 wherein the method further includes the steps of selecting a sulfur containing linking group;
    binding the sulfur containing linking group to the redox enzyme to form a linking group-enzyme component; and
    binding the linking group-enzyme component to the electrode material.

30. The analytical method of claim 29 wherein the method further includes the step of selecting a linking group with the following general formula (I):

$$Z-R^1-Q \qquad (I)$$

wherein:
    Z represents a sulfur containing moiety,
    Q represents a group selected from the group consisting of $X^1$ and P wherein $X^1$ is a functional group which forms a covalent bond with a moiety of at least one component and P is selected from the group consisting of proteins, polypeptides and polymers, each having at least one functional group $X^2$ which forms a covalent bond with a moiety of at least one component and $R^1$ represents a connecting group.

31. The analytical method of claim 30 wherein the method further includes the step of selecting the $X^1$ or $X^2$ linking group wherein $X^1$ and $X^2$ are independently selected from the group consisting of an amine group, a carboxyl group, $-N=C=S, -N=C=O$, aryl group and

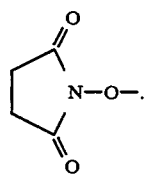

32. The analytical method of claim 31, wherein the method further includes the step of selecting an acyl group which has the formula $-R^a-CO-G$,
    wherein G is selected from the group consisting of OH, halogen and $OR^b$, and $R^a$ or $R^b$ being independently selected from the group consisting of $C_1-C_{12}$alkyl, $C_1-C_{12}$alkynyl, $C_1-C_{12}$ alkenyl and phenyl containing chains.

33. The analytical method of claim 30 wherein the method further includes the step of selecting a group P from the group consisting of polyamides and polypeptides with free amine or carboxyl groups.

34. The analytical method of claim 33 wherein the method further includes the step of selecting a group P from the group consisting of polylysine, polyglutamate and polyethyleneimine.

35. The analytical method claim 33 wherein P carries a plurality of functional groups $X^1$ wherein $X^1$ is a functional group which forms a covalent bond with a moiety of at least one component.

36. The analytical method of claim 30 wherein $R^1$ is selected from the group consisting of a covalent bond, alkylene chain, alkenyl chain, alkynyl chain and phenyl containing chain.

37. The analytical method of claim 30 wherein $R^1$ is selected from the group consisting of a chemical bond, and a group having the following formula (II a), (II b) and (III):

$$R^2-\overset{\overset{\displaystyle A}{\|}}{C}- \qquad (IIa)$$

$$R^2-NH- \qquad (IIb)$$

$$-R^3-NH-\overset{\overset{\displaystyle A}{\|}}{C}-NH-Ph-CH=CH-Ph-NH-\overset{\overset{\displaystyle B}{\|}}{C}- \qquad (III)$$

wherein:
    $R^2$ and $R^3$ may be the same or different and are selected from the group consisting of a covalent bond and straight or branched alkylene, alkenylenes, alkynylene molecules having 1–12 carbon atoms;

A and B may be the same or different and are independently selected from the group consisting of oxygen and sulfur; and Ph is a phenyl which is selected from the group consisting of phenyl, alkylphenyl, polyalkylphenyl, phenyl sulfate, alkylphenyl sulfate, polyalkylphenyl sulfate, polyalkylphenyl polysulfate.

38. An analytical method for determining the presence or concentration of analyte in a liquid medium comprising the steps of;
providing an electrobiochemical system comprising a test electrode which has a sulfur containing moiety;
providing an electron mediator;
chemisorbing the election mediator onto the test electrode;
introducing a liquid medium with an analyte to the electrobiochemical system;
providing a redox enzyme for oxidizing or reducing the analyte and for interacting with the electron mediator;
introducing the redox enzyme into the liquid medium;
applying a constant or alternate electric potential to the test electrode so that electrons pass between the mediator group, test electrodes and redox enzyme;
allowing the enzyme to catalyze the reaction of the analyte; and
measuring the concentration of the analyte.

39. The method of claim 38 wherein the method further includes the steps of selecting an electron mediator group;
reacting said electron mediator group with the redox enzyme to form a redox enzyme-electron mediator group; and introducing the redox enzyme-electron mediator complex into the liquid medium.

40. The method of claim 39 wherein the analyte concentration is measured by measuring the flow of electric charge.

41. The method of claim 39 wherein the analyte concentration is measured by measuring the concentration of the redox reaction product in the liquid medium.

42. An analytical method for determining the presence or concentration of analyte in a liquid medium comprising the steps of;
providing an electrobiochemical system comprising a test electrode which has a sulfur containing moiety;
providing an electron mediator;
chemisorbing the election mediator onto the test electrode;
introducing a liquid medium with an analyte to the electrobiochemical system;
providing a redox enzyme for oxidizing or reducing the analyte and for interacting with the electron mediator;
introducing the redox enzyme into the liquid medium;
applying a constant or alternate electric potential to the test electrode so that electrons pass between the mediator group, test electrodes and redox enzyme;
allowing the enzyme to catalyze the reaction of the analyte; and
measuring the concentration of the analyte by measuring the flow of electric charge.

43. An analytical method for determining the presence or concentration of analyte in a liquid medium comprising the steps of;
providing an electrobiochemical system comprising a test electrode which has a sulfur containing moiety;
providing an electron mediator;
chemisorbing the election mediator onto the test electrode;
introducing a liquid medium with an analyte to the electrobiochemical system;
providing a redox enzyme for oxidizing or reducing the analyte and for interacting with the electron mediator;
introducing the redox enzyme into the liquid medium;
applying a constant or alternate electric potential to the test electrode so that electrons pass between the mediator group, test electrodes and redox enzyme;
allowing the enzyme to catalyze the reaction of the analyte; and
measuring the concentration of the analyte by measuring the concentration of the redox reaction product in the liquid medium.

44. An analytical method for determining the presence or concentration of an analyte in a liquid medium comprising the steps of:
selecting an appropriate electrobiochemical system, the electrobiochemical system comprising selecting a test electrode which has chemisorption of sulfur containing moieties;
selecting a redox enzyme, the redox enzyme selectively converts the analyte to a product;
binding the redox enzyme to the test electrode;
selecting an electron mediator material which transfers electrons to and from the redox enzyme and test electrode;
introducing a liquid medium with an analyte to the electrobiochemical system;
applying a constant or alternating electric potential to the test electrode so that electrons pass between the redox enzyme and the test electrode allowing the redox enzyme to catalyze the reaction of the analyte; and
measuring the concentration of the analyte by measuring the flow of electron charge.

45. An analytical method for determining the presence or concentration of an analyte in a liquid medium comprising the steps of:
selecting an appropriate electrobiochemical system, the electrobiochemical system comprising selecting a test electrode which has chemisorption of sulfur containing moieties;
selecting a redox enzyme, the redox enzyme selectively converts the analyte to a product;
binding the redox enzyme to the test electrode;
selecting an electron mediator material which transfers electrons to and from the redox enzyme and test electrode;
introducing a liquid medium with an analyte to the electrobiochemical system;
applying a constant or alternating electric potential to the test electrode so that electrons pass between the redox enzyme and the test electrode allowing the redox enzyme to catalyze the reaction of the analyte; and
measuring the concentration of the analyte by measuring the concentration of the redox reaction product in the liquid medium.

* * * * *

UNITED STATES PATENT AND TRADEMARK OFFICE
CERTIFICATE OF CORRECTION

PATENT NO. : 5,443,701
DATED : August 22, 1995
INVENTOR(S) : Itamar WILLNER et al.

It is certified that error appears in the above-indentified patent and that said Letters Patent is hereby corrected as shown below:

Claim 1, line 8, "converts" should read --converting--.
      line 15, "electric" should read --electrical--.
Claim 5, line 3, "formulae" should read --formula--.
Claim 7, line 2, "have" should read --has--.
Claim 10, line 1, "material" should read --material that--.
      last line, "convened" should read --converted--.
Claim 18, line 3, "formula" should read --formulae--.
Claim 19, line 1, "anyone" should read --any one--.
Claim 23, line 4 "same of" should read --same or--.
Claim 25, line 3, "catalyst" should read --catalyse--.
Claim 31, line 5, "aryl" should read --acyl--.
Claim 35, line 1, "method claim" should read --method of--.
Claim 38, line 7, "election" should read --electron--.
Claim 42, line 7, "election" should read --electron--.
Claim 43, line 7, "election" should read --electron--.
Claim 45, line 6, "chemisorption of" should read --chemisorbed--.

Signed and Sealed this

Tenth Day of February, 1998

*Attest:*

BRUCE LEHMAN

*Attesting Officer*      *Commissioner of Patents and Trademarks*